US012594025B2

(12) United States Patent
    Javed

(10) Patent No.: US 12,594,025 B2
(45) Date of Patent: Apr. 7, 2026

(54) APPARATUS AND METHODS FOR SCREENING, DIAGNOSIS AND MONITORING OF RESPIRATORY DISORDERS

(71) Applicant: ResMed Pty Ltd, Bella Vista (AU)

(72) Inventor: Faizan Javed, Sydney (AU)

(73) Assignee: ResMed Pty Ltd (AU)

( * ) Notice: Subject to any disclaimer, the term of this patent is extended or adjusted under 35 U.S.C. 154(b) by 0 days.

(21) Appl. No.: 18/637,942

(22) Filed: Apr. 17, 2024

(65) Prior Publication Data

US 2024/0398336 A1     Dec. 5, 2024

Related U.S. Application Data

(63) Continuation of application No. 17/752,193, filed on May 24, 2022, now Pat. No. 11,986,314, which is a (Continued)

(30) Foreign Application Priority Data

Oct. 11, 2016    (AU) ................................ 2016904105

(51) Int. Cl.
    *A61B 5/00*         (2006.01)
    *A61B 5/01*         (2006.01)
    (Continued)

(52) U.S. Cl.
    CPC .............. *A61B 5/4818* (2013.01); *A61B 5/01* (2013.01); *A61B 5/02055* (2013.01);
    (Continued)

(58) Field of Classification Search
    CPC ....... A61B 5/4818; A61B 5/01; A61B 5/0533; A61B 5/0816; A61B 5/1116;
    (Continued)

(56) References Cited

U.S. PATENT DOCUMENTS 7,297,119 B2    11/2007    Westbrook et al.
7,570,979 B2     8/2009    Cooper
                (Continued)

FOREIGN PATENT DOCUMENTS

WO    2005018737 A1    3/2005
WO    2006048852 A1    5/2006
                (Continued)

OTHER PUBLICATIONS

EP Search Report dated Feb. 13, 2020 for EP Application No. 17860941.

(Continued)

*Primary Examiner* — Carl H Layno
*Assistant Examiner* — Anh-Khoa N Dinh
(74) *Attorney, Agent, or Firm* — Botos Churchill IP Law LLP

(57)                    ABSTRACT

A device that may include, or communicate with, sensors such as an electrocardiogram (ECG) sensor, an accelerometer, and/or a photoplethysmograph (PPG) detects sleep-disordered breathing (SDB) events of a patient based on signals from the sensors. The device may have a processor configured to make the detection(s). In an example, the processor may access a memory with processor control instructions. The instructions may be adapted to configure the processor to carry out the detection methodology. The method may include analysing an ECG data of the patient from a signal generated by the ECG sensor, pulse oximetry data of the patient from a signal generated by the PPG, and a three-dimensional (3D) accelerometry data of the patient from a signal generated by the accelerometer to detect the SDB events. The device and methods may be used for screening, diagnosis and monitoring of respiratory disorders.

20 Claims, 16 Drawing Sheets

Related U.S. Application Data continuation of application No. 16/340,905, filed as application No. PCT/AU2017/051091 on Oct. 10, 2017, now Pat. No. 11,350,874.

(51) Int. Cl.

| | |
|---|---|
| *A61B 5/0205* | (2006.01) |
| *A61B 5/0533* | (2021.01) |
| *A61B 5/08* | (2006.01) |
| *A61B 5/11* | (2006.01) |
| *A61B 5/113* | (2006.01) |
| *A61B 5/1455* | (2006.01) |
| *A61B 5/316* | (2021.01) |
| *A61B 5/318* | (2021.01) |
| *A61B 5/349* | (2021.01) |
| *A61B 7/04* | (2006.01) |

(52) U.S. Cl.
CPC .......... *A61B 5/0533* (2013.01); *A61B 5/0816* (2013.01); *A61B 5/1116* (2013.01); *A61B 5/1118* (2013.01); *A61B 5/1126* (2013.01); *A61B 5/14551* (2013.01); *A61B 5/316* (2021.01); *A61B 5/318* (2021.01); *A61B 5/349* (2021.01); *A61B 5/4812* (2013.01); *A61B 5/6823* (2013.01); *A61B 5/6833* (2013.01); *A61B 5/721* (2013.01); *A61B 5/7264* (2013.01); *A61B 5/7278* (2013.01); *A61B 5/0826* (2013.01); *A61B 5/113* (2013.01); *A61B 7/04* (2013.01); *A61B 2562/0204* (2013.01); *A61B 2562/0219* (2013.01); *A61B 2562/0271* (2013.01)

(58) Field of Classification Search
CPC . A61B 5/1118; A61B 5/1126; A61B 5/14551; A61B 5/4812; A61B 5/6823; A61B 5/6833; A61B 5/721; A61B 5/7264; A61B 5/7278; A61B 2562/0204; A61B 2562/0219; A61B 2562/0271; A61N 1/3601; A61N 1/36139; A61N 1/36514; A61N 1/36542; A61N 1/36578; A61N 1/36053; A61N 1/36114; A61N 1/36117; A61N 1/0556; A61N 1/3611; A61N 1/36135; A61N 1/37247; A61N 1/37264; A61N 1/046; A61N 1/362; A61N 1/39044
See application file for complete search history.

(56) References Cited

U.S. PATENT DOCUMENTS

| | | | |
|---|---|---|---|
| 8,622,922 B2 | 1/2014 | Banet et al. | |
| 2005/0109339 A1* | 5/2005 | Stahmann .......... | A61N 1/36542 |
| | | | 128/204.23 |
| 2006/0293608 A1 | 12/2006 | Rothman et al. | |
| 2007/0032733 A1* | 2/2007 | Burton ................. | A61B 5/7264 |
| | | | 600/509 |
| 2007/0060802 A1* | 3/2007 | Ghevondian ........ | A61B 5/6831 |
| | | | 600/301 |
| 2007/0276439 A1 | 11/2007 | Miesel et al. | |
| 2008/0009685 A1 | 1/2008 | Kim et al. | |
| 2008/0127978 A1 | 6/2008 | Rubin et al. | |
| 2008/0319513 A1* | 12/2008 | Pu ...................... | A61N 1/36139 |
| | | | 607/62 |
| 2009/0076364 A1* | 3/2009 | Libbus ................. | A61B 5/282 |
| | | | 607/20 |
| 2009/0076405 A1 | 3/2009 | Amurther | |
| 2009/0203972 A1 | 8/2009 | Heneghan et al. | |
| 2010/0100004 A1 | 4/2010 | Van Someren | |
| 2011/0034811 A1 | 2/2011 | Naujokat et al. | |
| 2011/0066037 A1 | 3/2011 | Banet et al. | |
| 2011/0295142 A1 | 12/2011 | Chakravarthy et al. | |
| 2012/0330173 A1* | 12/2012 | Park ..................... | A61B 5/18 |
| | | | 600/509 |
| 2014/0078229 A1 | 3/2014 | Jackson et al. | |
| 2014/0221849 A1 | 8/2014 | Farringdon et al. | |
| 2014/0278229 A1 | 9/2014 | Hong et al. | |
| 2015/0057512 A1 | 2/2015 | Kapoor | |
| 2015/0238103 A1 | 8/2015 | Younes | |
| 2015/0313484 A1 | 11/2015 | Burg et al. | |
| 2016/0287122 A1 | 10/2016 | Heneghan | |

FOREIGN PATENT DOCUMENTS

| | | |
|---|---|---|
| WO | 2009024273 A1 | 2/2009 |
| WO | 2010134068 A1 | 11/2010 |
| WO | 2012024106 A2 | 2/2012 |
| WO | 2013177621 A1 | 12/2013 |

OTHER PUBLICATIONS

Frank H. Wilhelm, Ph.D., et al., "The LifeShirt: An Advanced System for Ambulatory Measurement of Respiratory and Cardiac Function" 22 pages (2003).

International Search Report issued in AU application No. PCT/AU2017/051091 on Mar. 28, 2018.

Kevin T. Sweeney, et al. "Identification of Sleep Apnea Events using Discrete Wavelet Transform of Respiration, ECG and Accelerometer Signals" 6 pages (2013).

Office action from corresponding EP Application No. 17860941.8-1113 dated Mar. 27, 2023.

Thomas Brack, et al. "Cheyne-Stokes Respiration in Patients with Heart Failure: Prevalence, Causes, Consequences and Treatments" pp. 165-176 (2012).

Philip de Chazal /Conor Heneghan paper,"Automated processing of the Single-Lead Electrocardiogram for the Detecion of Obstructive Sleep Apnoea" IEEE Trans-Biomed, vol. 50, No. 6, Jun. 2003, pp. 686-696.

Foo, Jong Yong Abdiel, et al., Development of a Home Screening System for Pediatric Respiratory Sleep Studies, Telemedicine and e-Health, vol. 12, No. 6, Jan. 25, 2007, pp. 698-701.

* cited by examiner

Nasal cavity

Oral cavity

Larynx

Vocal folds

Oesophagus

Trachea

Bronchus

Lung

Heart

Diaphragm

Alveolar sacs

7100

1

APPARATUS AND METHODS FOR SCREENING, DIAGNOSIS AND MONITORING OF RESPIRATORY DISORDERS

1 CROSS-REFERENCE TO RELATED APPLICATIONS

The present application is a continuation of U.S. application Ser. No. 17/752,193, filed May 24, 2022, issued as U.S. Pat. No. 11,986,314, which is a continuation of U.S. application Ser. No. 16/340,905, filed Apr. 10, 2019, issued as U.S. Pat. No. 11,350,874, which is a national phase entry under 35 U.S.C. § 371 of International Application No. PCT/AU2017/051091, filed Oct. 10, 2017, published in English, which claims priority from Australian Application No. 2016904105, filed Oct. 11, 2016, all of which are incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange.

The nose and mouth form the entrance to the airways of a patient. The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

2.2.2 Therapy

Various therapies, such as Continuous Positive Airway Pressure (CPAP) therapy, non-invasive ventilation (NIV) and invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

The above-mentioned therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, and a patient interface.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.4 Screening/Diagnosis/Monitoring Systems

Screening and diagnosis generally describe the identification of a disorder from its signs and symptoms. Screening typically gives a true/false result indicating whether or not a patient's disorder is severe enough to warrant further investigation, while diagnosis may result in clinically actionable information. Screening and diagnosis tend to be one-off processes, whereas monitoring the progress of a disorder can continue indefinitely. Some screening/diagnosis systems are suitable only for screening/diagnosis, whereas some may also be used for monitoring.

Polysomnography (PSG) is a conventional system for diagnosis/monitoring of cardio-pulmonary disorders, and typically involves expert clinical staff to apply the system. PSG typically involves the placement of 15 to 20 contact sensors on a person in order to record various biosignals such as electroencephalography (EEG), electrocardiography (ECG), electrooculography (EOG), electromyography (EMG), etc. PSG for sleep disordered breathing has involved two nights of observation of a patient in a clinic, one night of pure diagnosis and a second night of titration of treatment parameters by a clinician. Clinical experts may be able to diagnose or monitor patients adequately based on visual observation of PSG signals. However, there are circumstances where a clinical expert may not be available, or a clinical expert may not be affordable. PSG is therefore expensive and inconvenient. In particular it is unsuitable for in-home diagnosis/monitoring.

A more convenient screening/diagnosis/monitoring system for home use comprises a nasal cannula, a pressure sensor, a processing device, and recording means. A nasal cannula is a device comprising two hollow open-ended projections that are configured to be inserted non-invasively a little way into a patient's nares so as to interfere as little as possible with the patient's respiration. The hollow projections are in fluid communication with a pressure transducer via a Y-shaped tube. The pressure transducer provides a data signal representative of the pressure at the entrance to the patient's nares (the nasal pressure). It has been shown that a nasal pressure signal is a satisfactory proxy for the nasal flow rate signal generated by a flow rate transducer in-line with a sealed nasal mask, in that the nasal pressure signal is comparable in shape to the nasal flow rate signal. The processing device may be configured to analyse the nasal pressure signal from the pressure transducer in real time or near real time to detect and classify SDB events in order to monitor the patient's condition. Screening or diagnosis may require similar analysis but not necessarily in real time or near real time. The recording means is therefore configured to record the nasal pressure signal from the pressure transducer for later off-line or "batch" analysis by the processing device for screening/diagnosis purposes.

However, such pressure-based systems are not always able to reliably distinguish CSR from the repeated occurrences of obstructive apneas characteristic of OSA. Other sensor modalities have therefore been employed to supplement or replace the nasal pressure signal in more sophisticated screening/diagnosis/monitoring systems. However, such systems start to resemble full PSG as more sensors are added, with all the above-mentioned disadvantages. It is desirable to utilise a combination of sensors that are as unobtrusive as possible while maintaining accuracy of SDB screening/diagnosis/monitoring.

3 BRIEF SUMMARY OF THE TECHNOLOGY

The present technology is directed towards providing medical devices used in the screening, diagnosis, or monitoring of respiratory disorders having one or more of improved comfort, cost, efficacy, ease of use and manufacturability.

Some versions of the present technology may include a device having an electrocardiogram (ECG) sensor; an accelerometer; and a photoplethysmograph (PPG). The device may also include a processor. The device may also include a memory. The memory may include processor control instructions adapted to configure the processor to detect sleep-disordered breathing (SDB) events of a patient. The processor, such as with the instructions, may be configured to control an analysis of ECG data of the patient from a signal generated by the ECG sensor, pulse oximetry data of the patient from a signal generated by the PPG, and three-dimensional (3D) accelerometry data of the patient from a signal generated by the accelerometer. The processor, such as with the instructions, may also be configured to detect the SDB events based on the analysis.

In some cases, the analysis may estimate a sleep stage of the patient from the ECG data. The device may also include a temperature sensor. The analysis that estimates the sleep stage may evaluate temperature data from a signal generated by the temperature sensor. The temperature data may represent temperature of skin of the patient. In some cases, the device may include a galvanic skin response (GSR) sensor. The analysis to estimate the sleep stage may evaluate sympathetic activity data of the patient from a signal generated by the GSR sensor. In some cases, with the instructions, the processor may be further configured to classify the detected SDB events into apneas and hypopneas, and/or into open and closed airway events.

In some cases, the device may include a galvanic skin response (GSR) sensor. With the instructions, the processor may be configured to classify the detected SDB events by evaluation of sympathetic activity data of the patient from a signal generated by the GSR sensor. The device may also include an acoustic sensor. With the instructions, the processor may be configured to classify the detected SDB events by evaluation of acoustic data representing heart sound of the patient from a signal generated by the acoustic sensor. In some versions, the device may be configured as a patch adapted to be worn on skin of a chest of the patient.

Some versions of the present technology may include a method of detecting sleep-disordered breathing (SDB) events of a patient. The method may include controlling, in one or more processors, an analysis of electrocardiogram (ECG) data of the patient from a signal generated by an ECG sensor, pulse oximetry data of the patient from a signal generated by a photoplethysmograph (PPG), and three-dimensional (3D) accelerometry data of the patient from a signal generated by an accelerometer. The method may include detecting, in the one or more processors, SDB events based on the analysis, to generate an output indication of SDB events.

In some cases, the analysis of the ECG data may include removing artefacts from the ECG data to produce artefact-removed ECG data. Removing artefacts from the ECG data may include identifying portions of the ECG data that differ from a typical portion. Analysing the ECG data may include estimating a sleep stage of the patient based on the artefact-removed ECG data. Estimating a sleep stage may include evaluating patient skin temperature data from a temperature signal generated by a temperature sensor. Estimating a sleep stage may include evaluating sympathetic activity data of the patient from a signal generated by a galvanic skin response (GSR) sensor. The analysis of the ECG data may include estimating a respiratory rate from the artefact-removed ECG data. The analysis of the ECG data may include extracting a respiratory-related component from the artefact-removed ECG data. The analysis of the 3D accelerometry data may include estimating a posture of the patient from the 3D accelerometry data. The analysis of the 3D accelerometry data may include estimating a respiratory effort of the patient from the 3D accelerometry data. The analysis of the 3D accelerometry data may include computing an activity index of the patient from the 3D accelerometry data. The activity index may represent gross bodily motion of the patient.

In some cases, the detecting of the SDB events may include: extracting features, and discriminating between normal breathing and SDB events by applying a classifier to the features. The method may include, in the one or more processors, classifying the detected SDB events into apneas and hypopneas, and into open and closed airway events. In some cases, the classifying the detected SDB events may evaluate the pulse oximetry data from the PPG. The classifying the detected SDB events may evaluate sympathetic activity data of the patient from a signal generated by a galvanic skin response (GSR) sensor. The classifying the detected SDB events may evaluate acoustic data representing heart sound of the patient from a signal generated by an acoustic sensor. The classifying the detected SDB events may include segmenting the acoustic data into phases of each heart cycle, and extracting heart sound features from the segmented acoustic data. The classifying the detected SDB events may use the heart sound features.

In some cases, the method may include detecting, in the one or more processors, Cheyne-Stokes respiration (CSR) from classified SDB events from the classifying. The detecting CSR may include template matching of a respiratory-related component extracted from the ECG data. The method may include controlling, with the one or more processors, (a) generating the signal by the ECG sensor, (b) generating the signal by the photoplethysmograph (PPG), and (c) generating the signal by the accelerometer. The method may include determining or controlling, with the one or more processors, a change to a therapy provided by a therapy device based on the output indication of SDB events.

In some cases, a processor-readable medium may have stored thereon processor-executable instructions which, when executed by a processor, cause the processor to detect detecting sleep-disordered breathing (SDB) events according to any of the methodologies described herein.

Some versions of the present technology may include a system. The system may include an electrocardiogram (ECG) sensor; an accelerometer; and a photoplethysmograph (PPG). The system may include one or more processors. The system may include a memory having processor control instructions adapted to configure the one or more processors to detect sleep-disordered breathing (SDB) events of a patient. The one or more processors, such as with the instructions, may be configured to control an analysis of ECG data of the patient from a signal generated by the ECG sensor, pulse oximetry data of the patient from a signal generated by the PPG, and three-dimensional (3D) accelerometry data of the patient from a signal generated by the accelerometer. The one or more processors, such as with the instructions, may be configured to detect the SDB events based on the analysis.

In some cases, the ECG sensor, the accelerometer, the PPG, the memory, and the one or more processors are co-located in one device. In some cases, the ECG sensor, the accelerometer, and the PPG are co-located in one device, and the one or more processors and the memory are located remotely from the device. In some cases, the device of the system may include a communication interface through which the device may be configured to communicate with the one or more processors. The device may be configured as a patch adapted to be worn on skin of a chest of the patient.

Some versions of the present technology may include an apparatus. The apparatus may include means for generating electrocardiogram (ECG) data of a patient. The apparatus may include means for generating three-dimensional (3D) accelerometry data of the patient. The apparatus may include means for generating pulse oximetry data of the patient. The apparatus may include means for analysing the ECG data of the patient, the pulse oximetry data of the patient, and the 3D accelerometry data of the patient to detect sleep-disordered breathing (SDB) events of the patient.

In some cases, the apparatus may include means for estimating sleep stage from the ECG data. The apparatus may include means for generating temperature data, wherein the means for estimating sleep stage estimates sleep stage based on the temperature data. The apparatus may include means for generating sympathetic activity data, wherein the means for estimating sleep stage estimates sleep stage based on the sympathetic activity data. The apparatus may include means for classifying detected SDB events. The apparatus may include means for generating heart sound data, wherein the means for classifying classifies the SDB events based on the heart sound data. The apparatus may include means for removing artefact from the ECG data. The apparatus may include means for mounting the apparatus to skin of a chest of the patient.

Another aspect of the present technology relates to apparatus and methods to analyse data from a patch device including ECG contacts, a three-axis accelerometer, an acoustic sensor, and a pulse oximeter, to detect and classify apneas and hypopneas and hence screen, diagnose and/or monitor SDB. As part of the analysis, the signal processing may estimate sleep/wake state. The patch sensor may also include a temperature sensor and a galvanic skin response (GSR) sensor whose signals are incorporated into the analysis to improve the accuracy.

In accordance with another aspect of the present technology, there is provided a device comprising: an electrocardiogram (ECG) sensor; an accelerometer; a photoplethysmograph (PPG); a processor; and a memory comprising instructions adapted to configure the processor to carry out a method of detecting sleep-disordered breathing (SDB) events of a patient. The method comprises analysing an ECG signal of the patient from the ECG sensor, pulse oximetry data of the patient from the PPG, and a three-dimensional (3D) accelerometry signal of the patient from the accelerometer to detect the SDB events.

In accordance with another aspect of the present technology, there is provided a method of detecting sleep-disordered breathing (SDB) events of a patient. The method comprises analysing an electrocardiogram (ECG) signal of the patient from an ECG sensor, pulse oximetry data of the patient from a photoplethysmograph (PPG), and a three-dimensional (3D) accelerometry signal of the patient from an accelerometer to detect the SDB events.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows a patient interface in the form of a nasal mask in accordance with one form of the present technology.

4.4 RPT Device

FIG. 4 shows an RPT device in accordance with one form of the present technology.

4.5 Humidifier

4.6 Breathing Waveforms

Figure 6A:
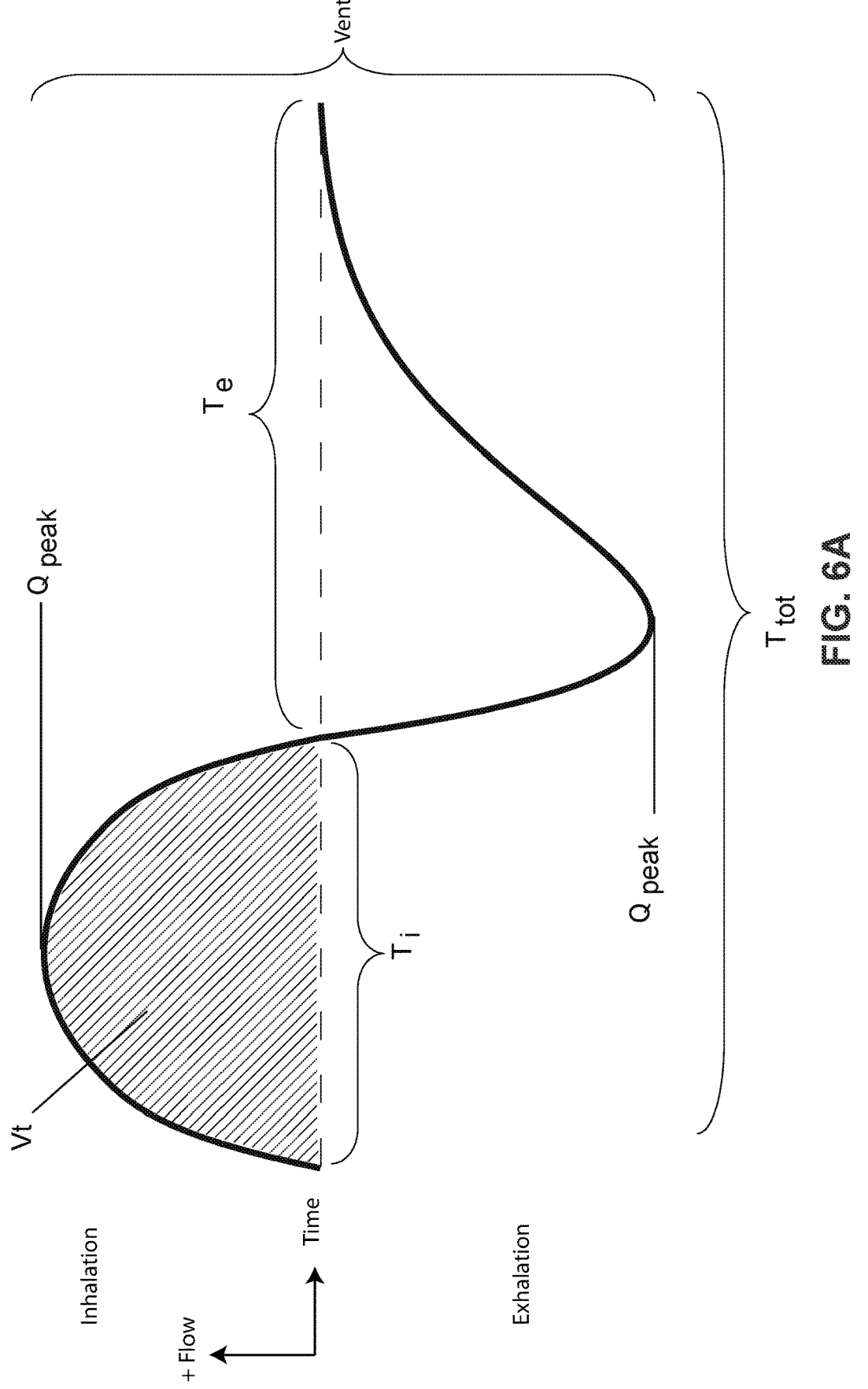

FIG. 6A shows a model typical breath waveform of a person while sleeping.

Figure 6B:
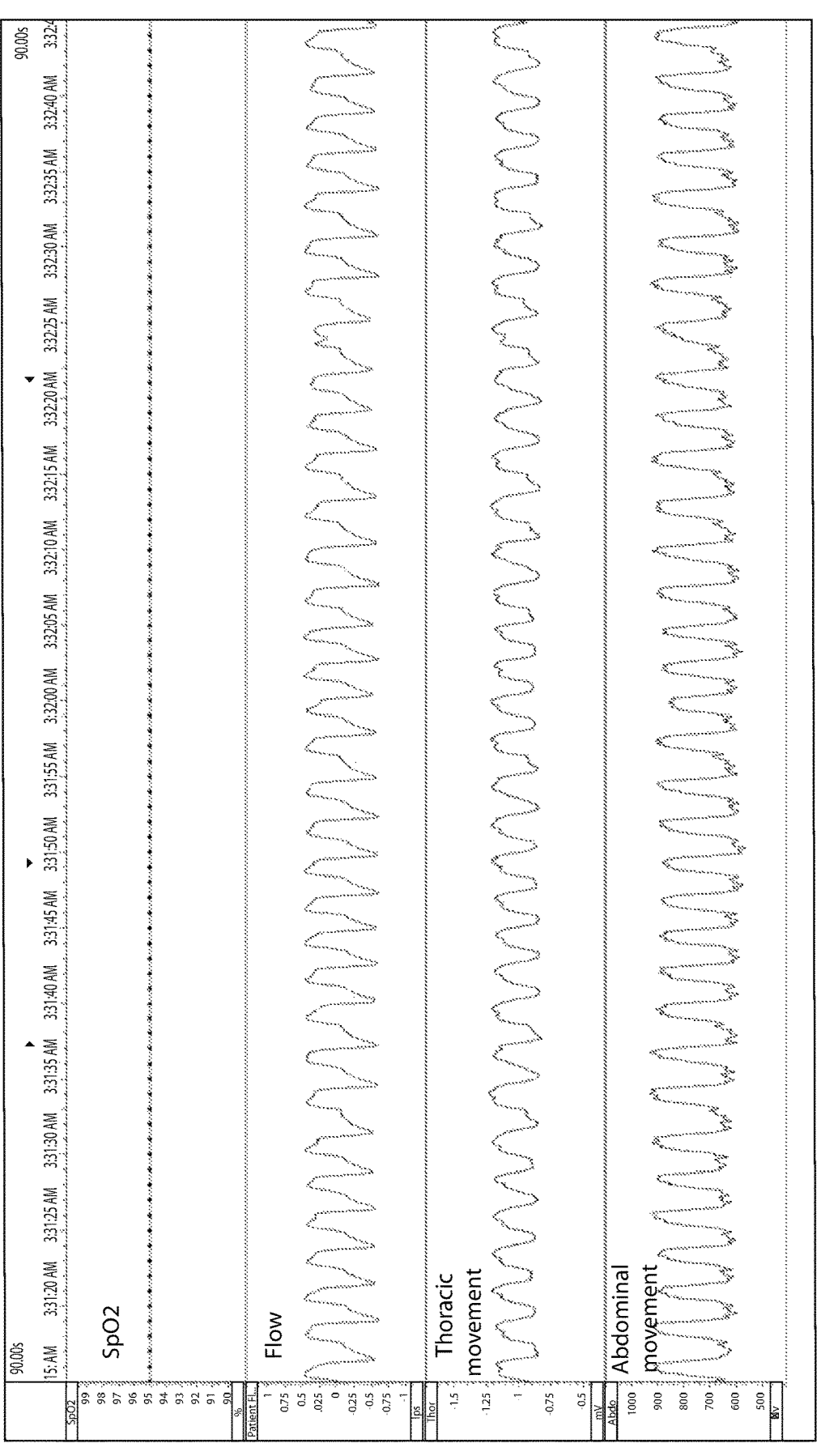

FIG. 6B shows a patient during Non-REM sleep breathing normally over a period of about ninety seconds.

Figure 6C:
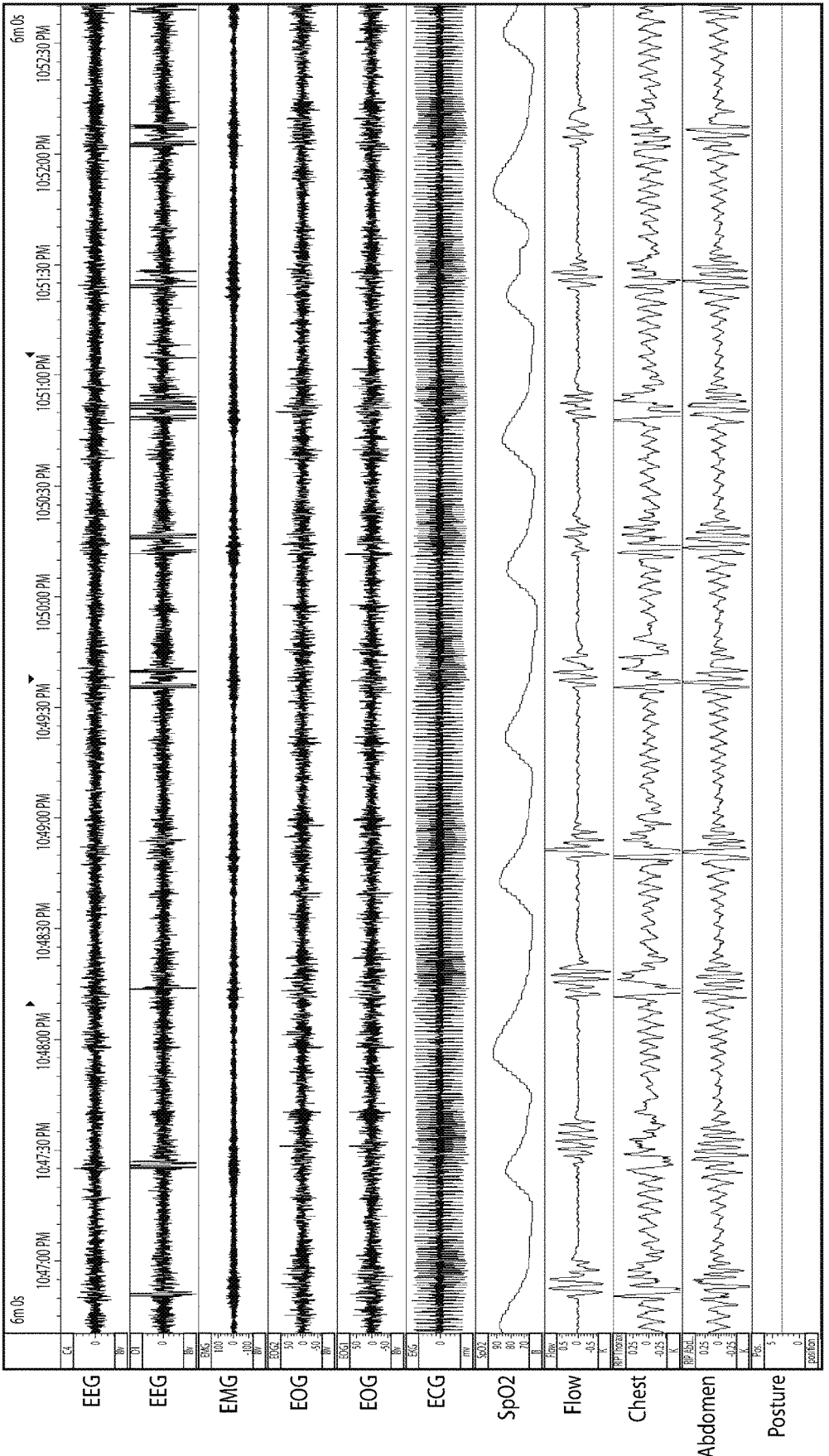

FIG. 6C shows polysomnography of a patient before treatment.

Figure 6D:
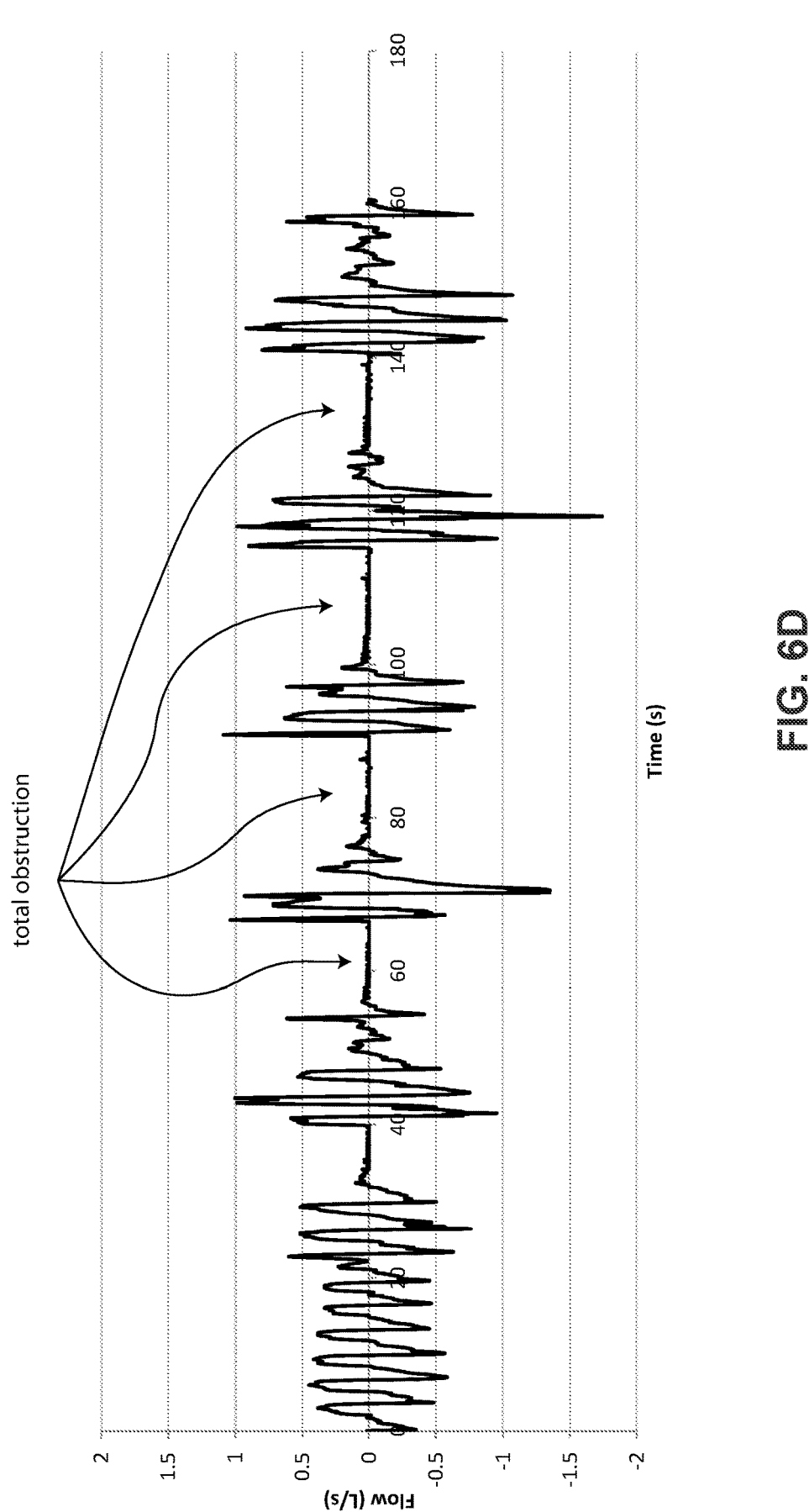

FIG. 6D shows patient flow data where the patient is experiencing a series of total obstructive apneas.

Figure 6E:
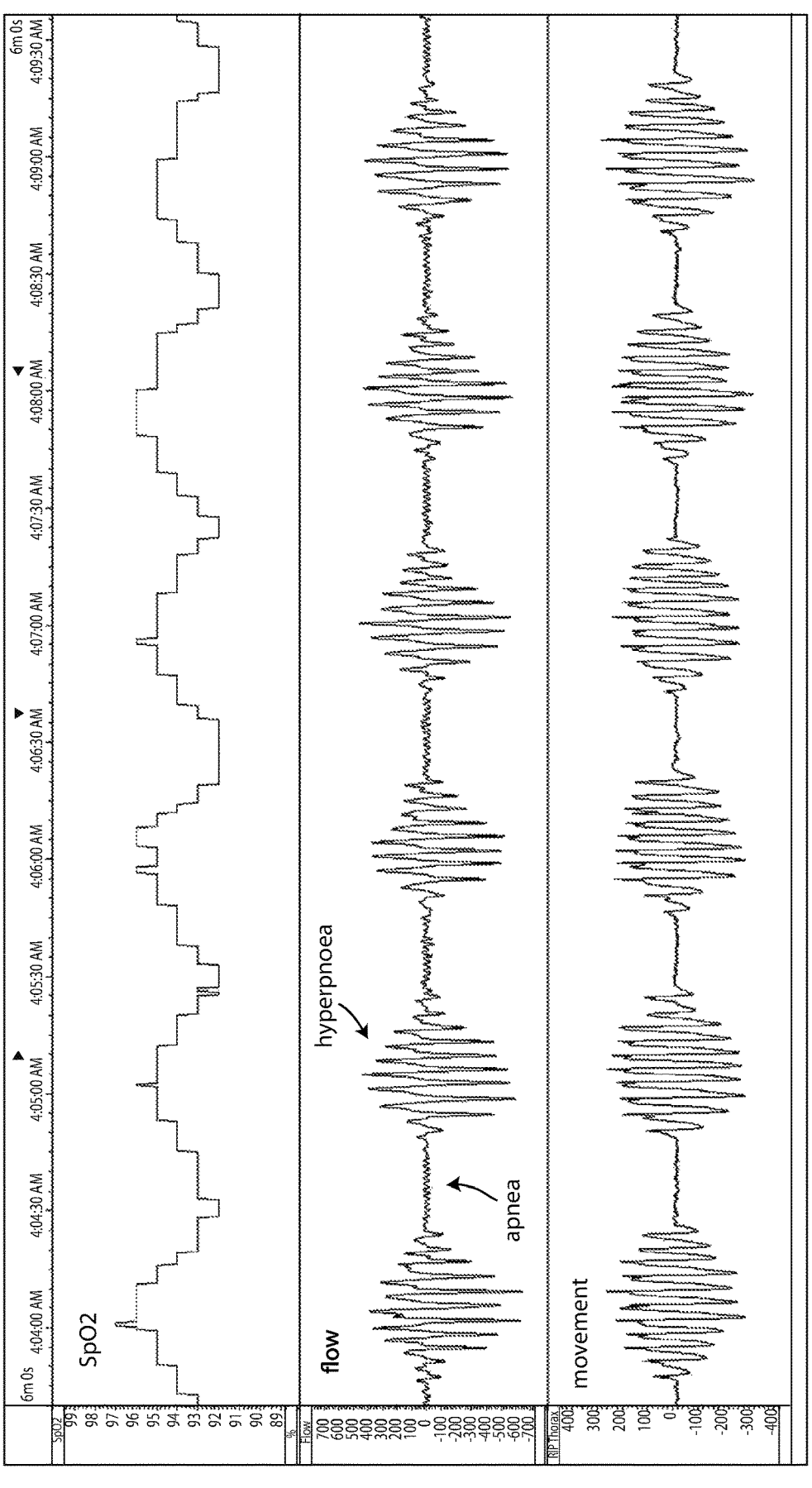

FIG. 6E shows patient data from a patient with Cheyne-Stokes respiration.

Figure 6F:
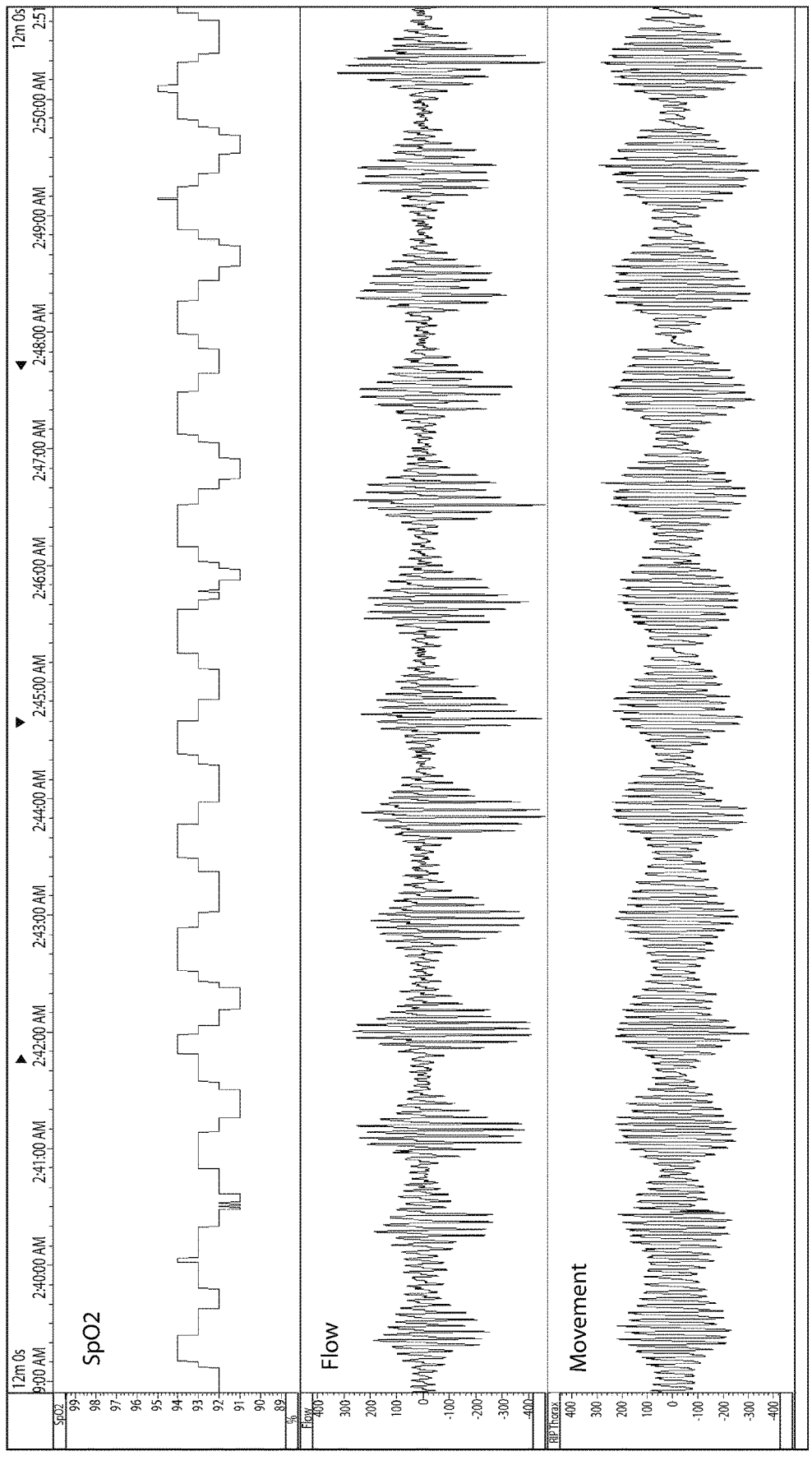

FIG. 6F shows patient data from a patient with another example of Cheyne-Stokes respiration, using the same three channels as in FIG. 6E.

4.7 Screening/Diagnosis/Monitoring Systems

Figure 7A:
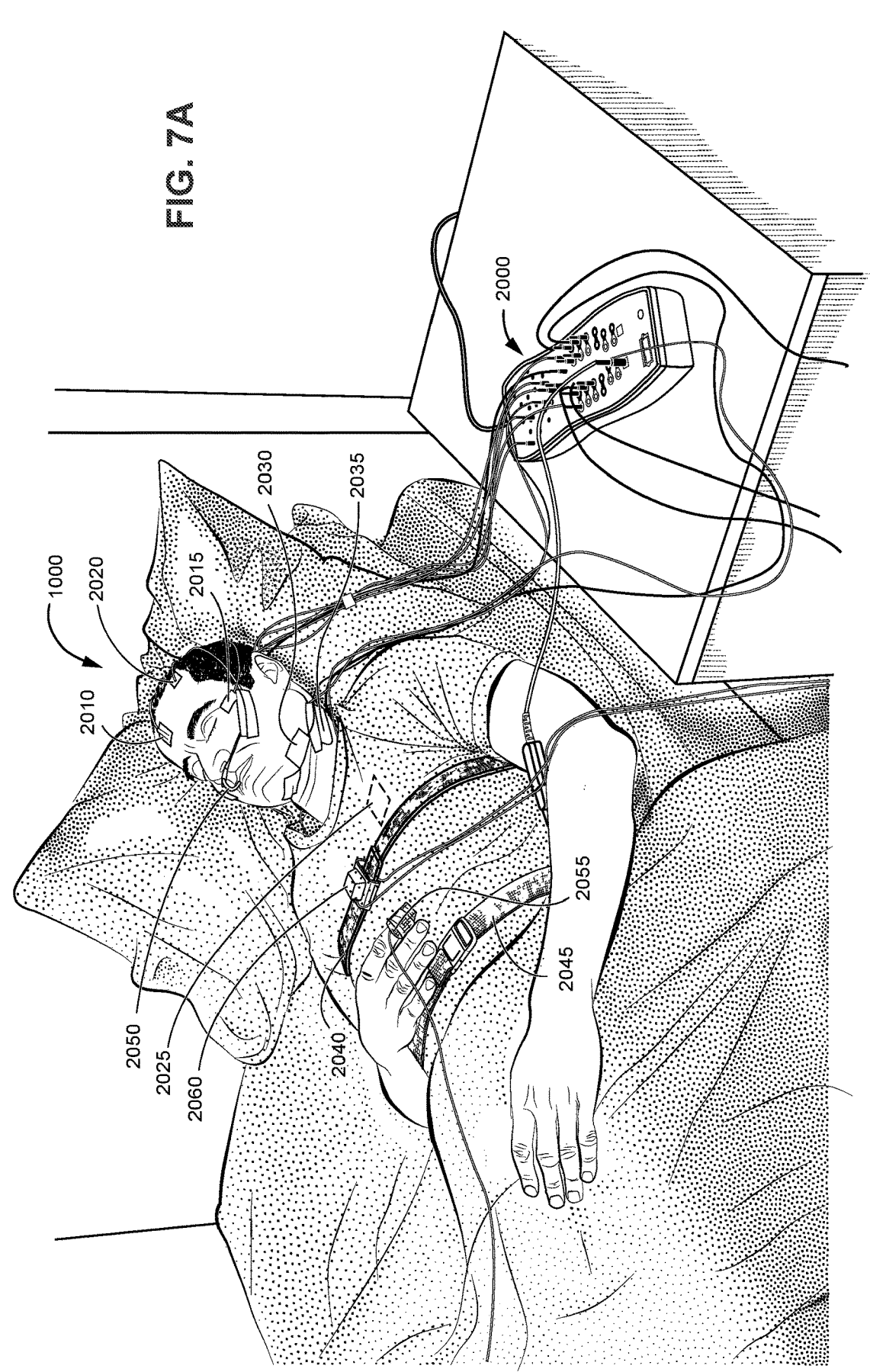

FIG. 7A shows a patient undergoing polysomnography (PSG).

Figure 7B:
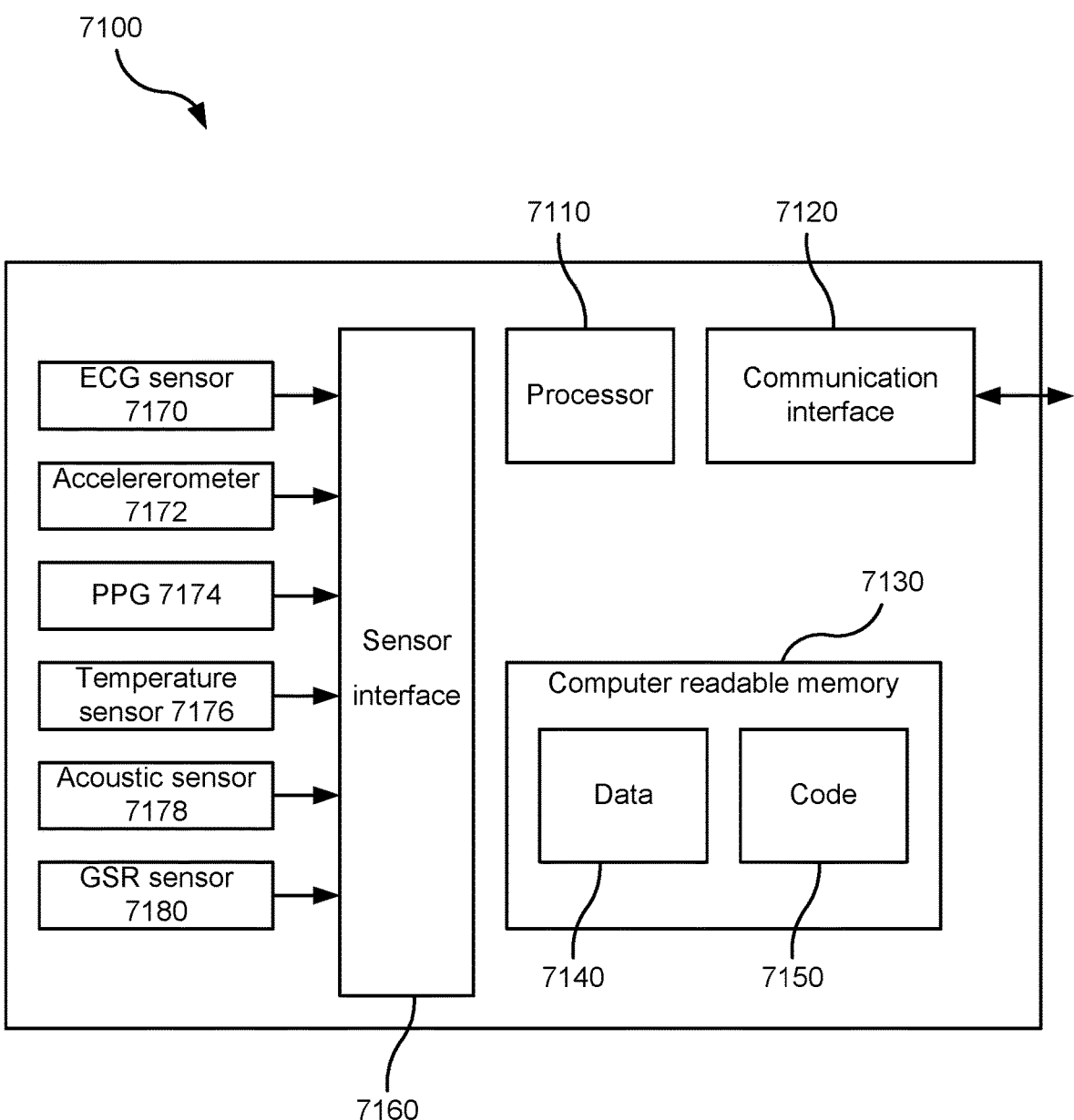

FIG. 7B is a block diagram illustrating a screening/diagnosis/monitoring device according to one form of the present technology.

Figure 8A:
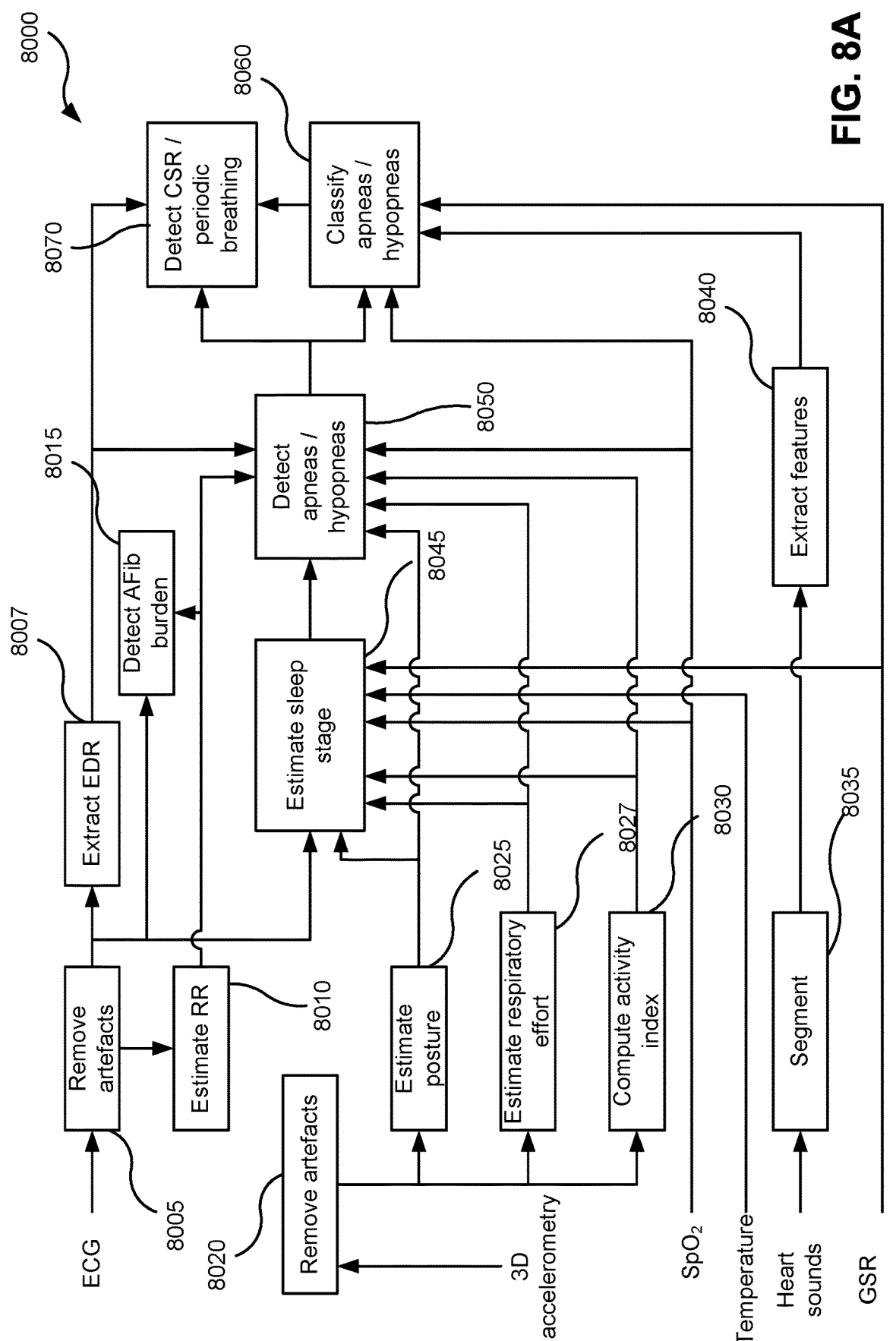

FIG. 8A is a flow chart illustrating a method of screening/diagnosing/monitoring SDB making use of the device of FIG. 7B in one form of the present technology.

Figure 8B:
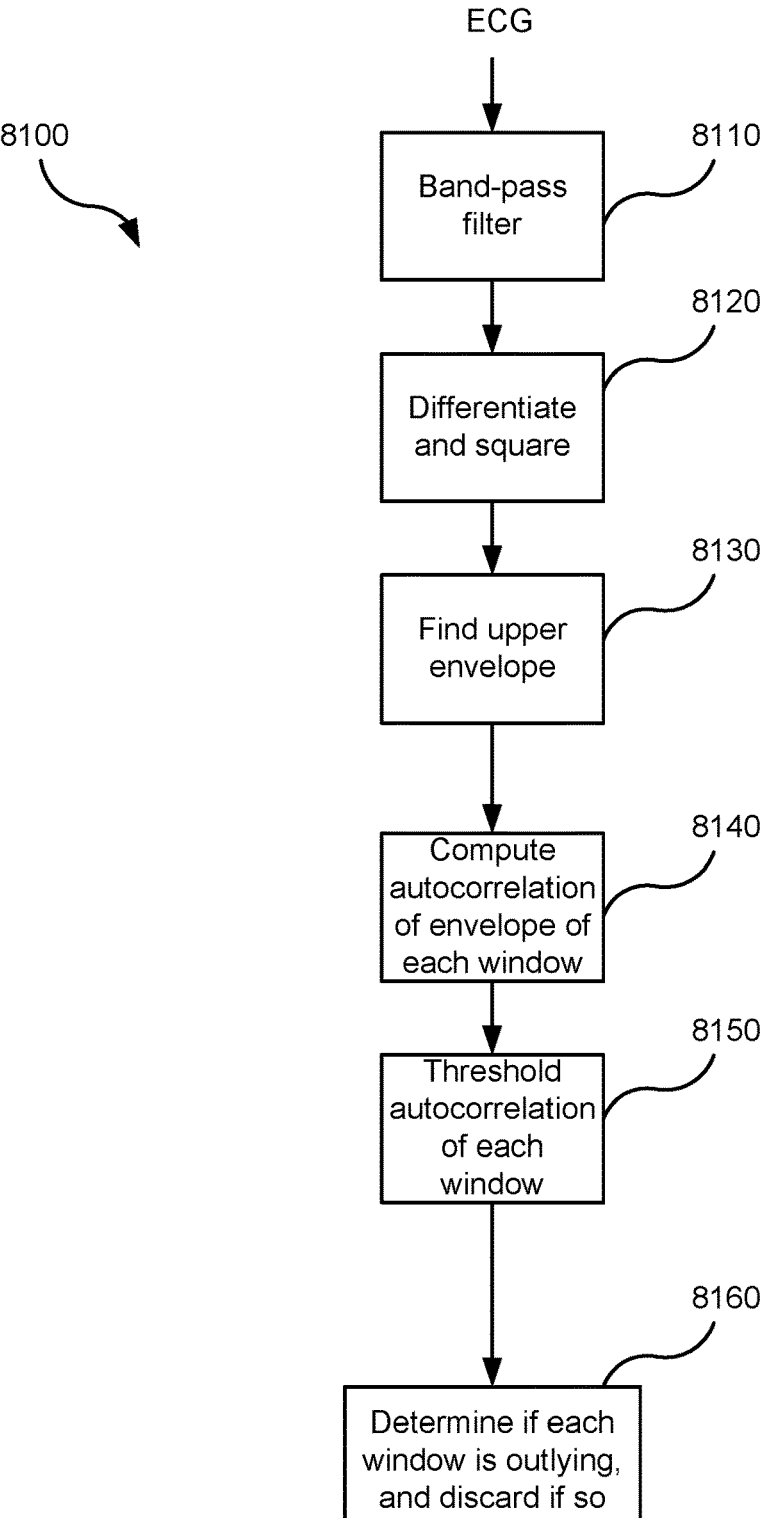

FIG. 8B is a flow chart illustrating a method that may be used to implement the artefact removal step of the method of FIG. 8 in one form of the present technology.

Figure 9:
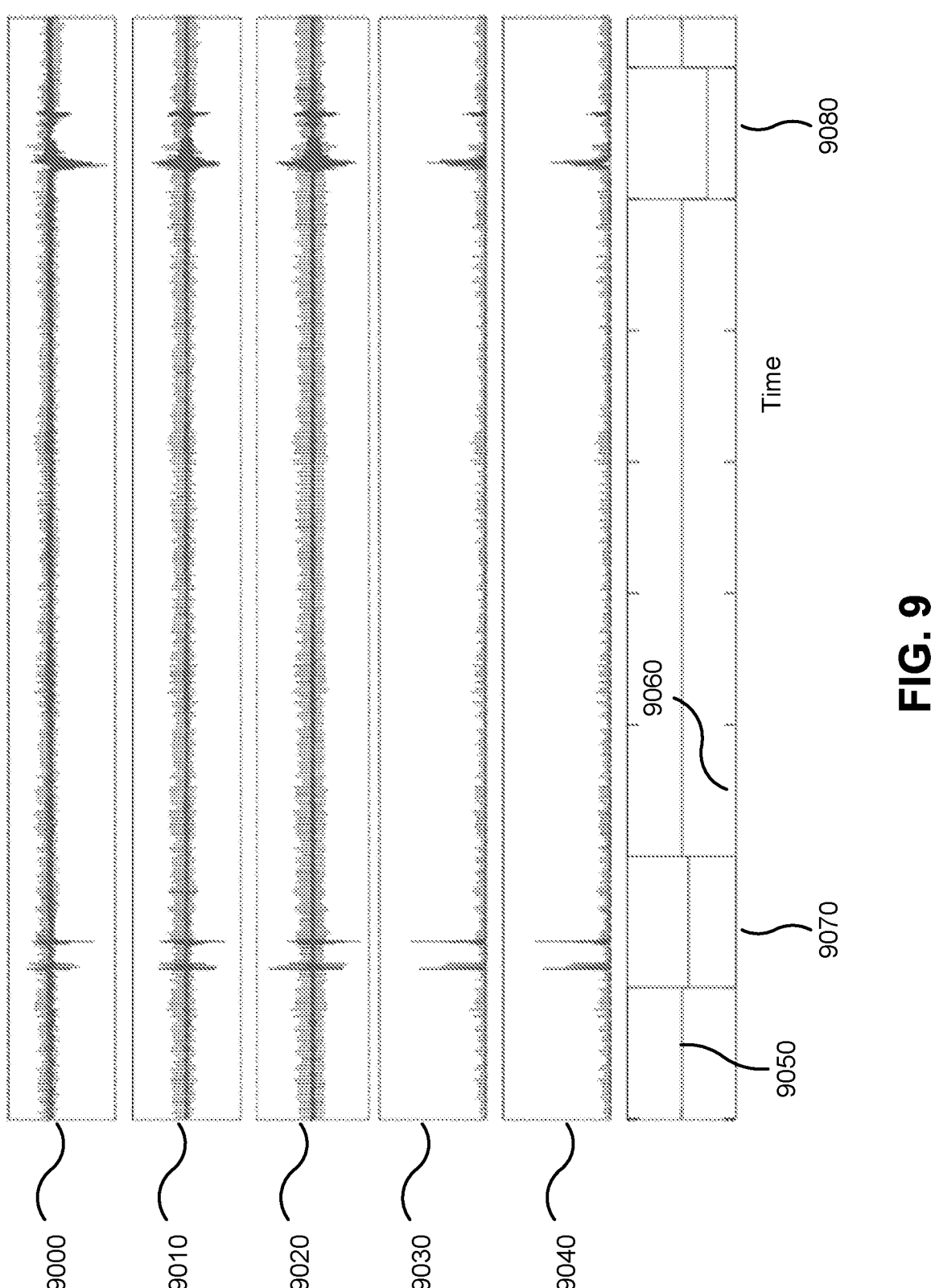

FIG. 9 is a graph illustrating the operation of the artefact removal method of FIG. 8B on an example ECG signal.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 RPT Device

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

The RPT device may have an external housing 4010, formed in two parts, an upper portion 4012 and a lower portion 4014. Furthermore, the external housing 4010 may include one or more panels 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112 and a pressure generator capable of supplying air at positive pressure (e.g., a blower 4142).

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210 and one or more input devices 4220. Electrical components 4200 may be mounted on a single Printed Circuit Board Assembly (PCBA) 4202.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

5.6 Humidifier

Figure 1:
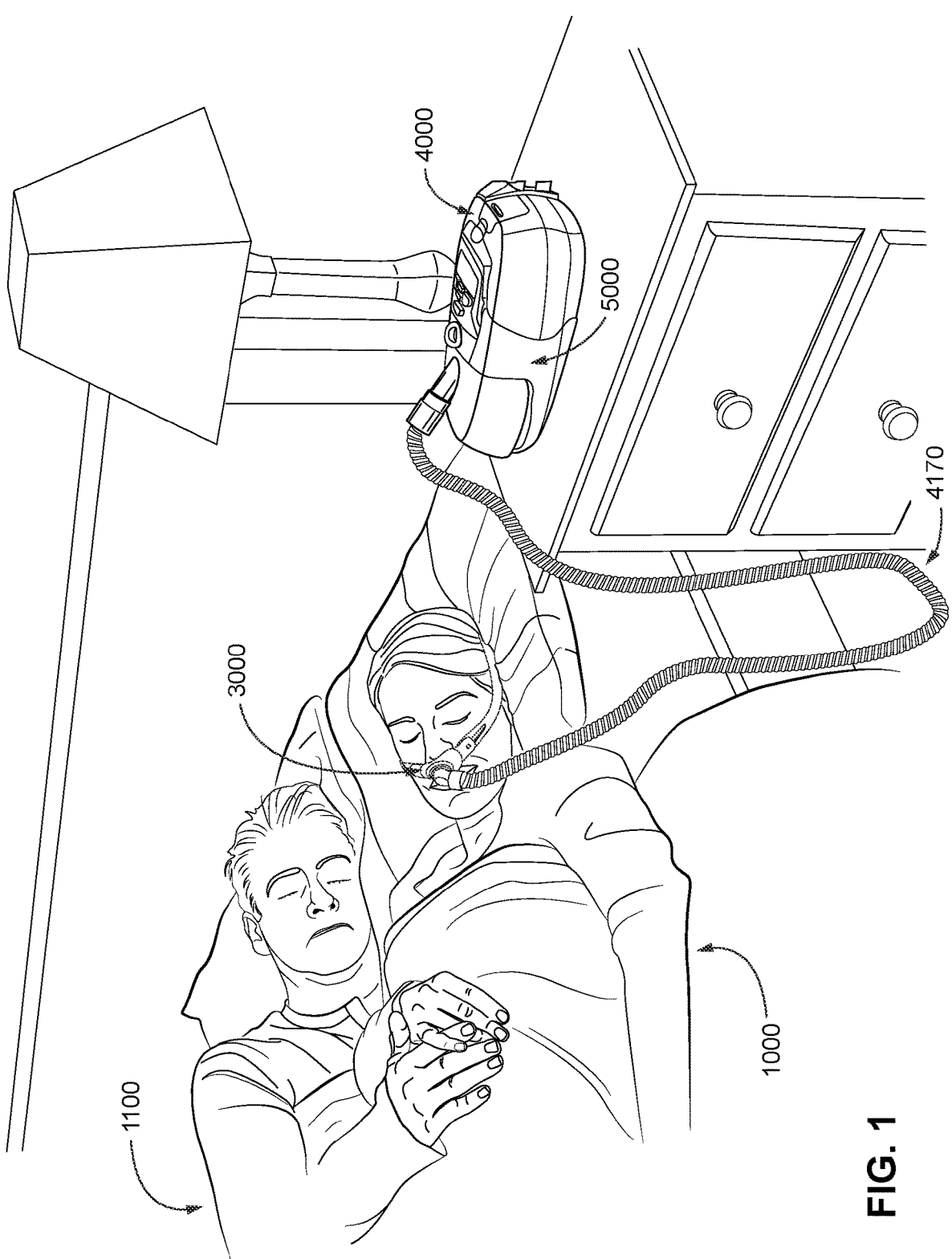
Figure 2:
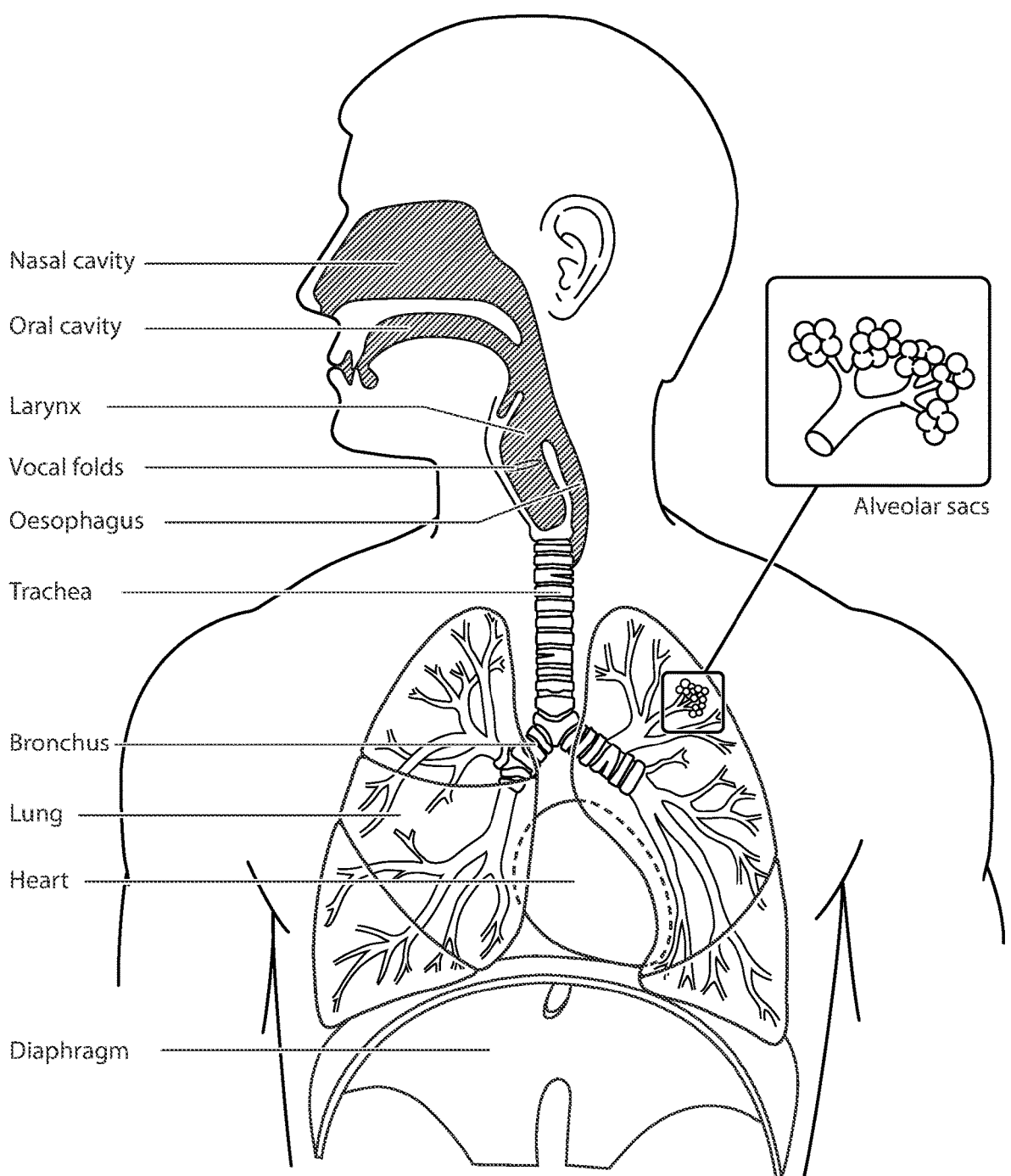
Figure 3:
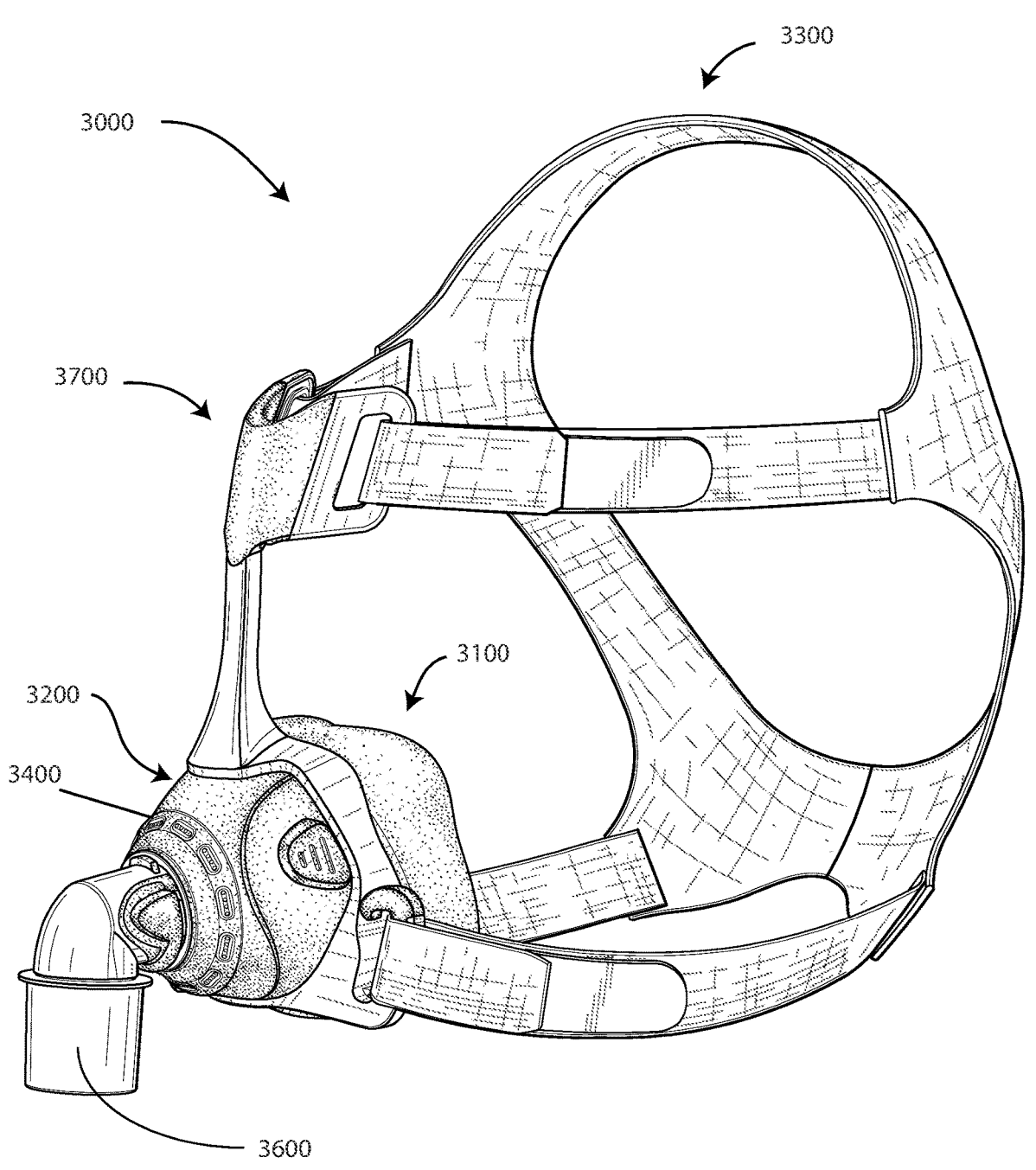
Figure 4:
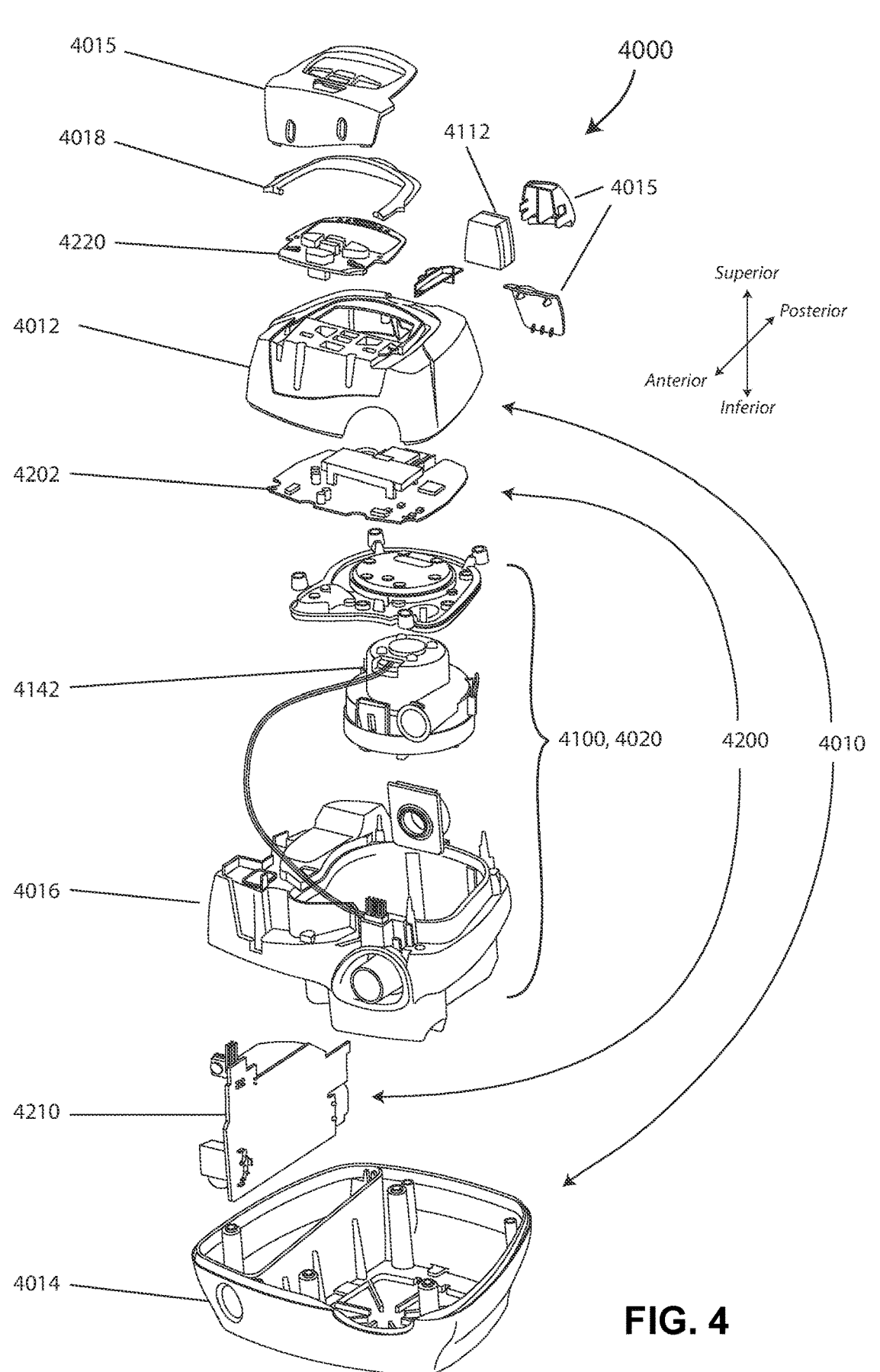
Figure 5A:
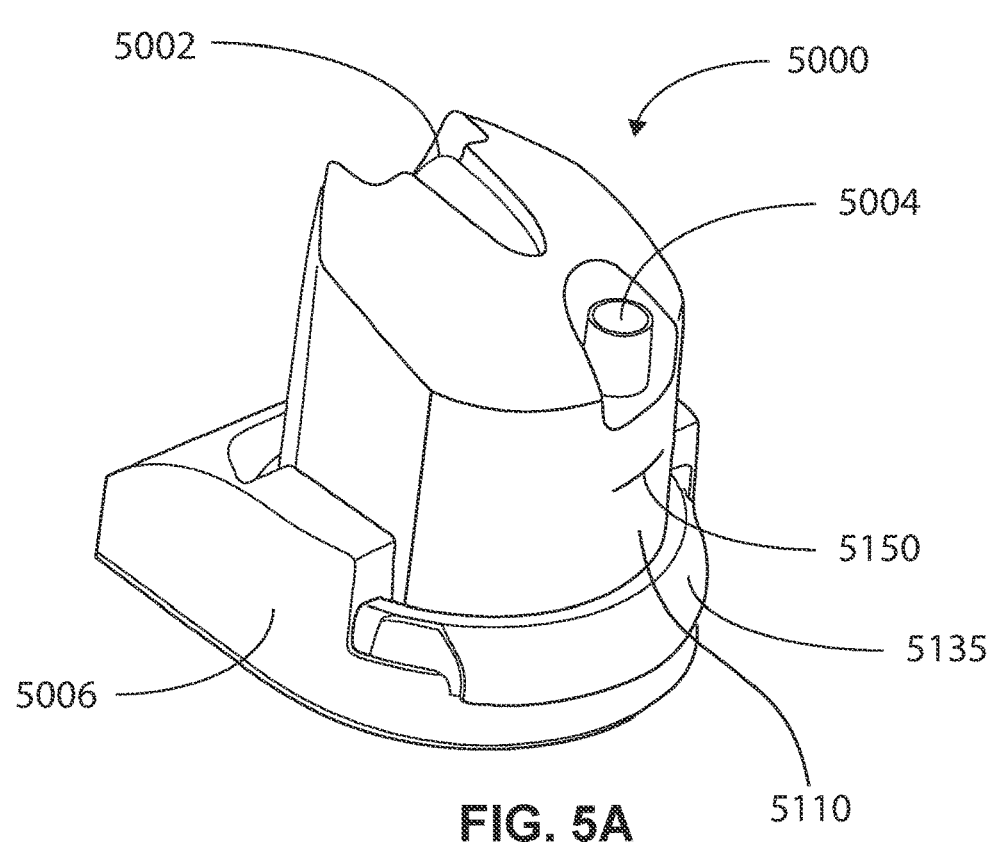
FIG. 5A shows an isometric view of a humidifier in accordance with one form of the present technology.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 5B:
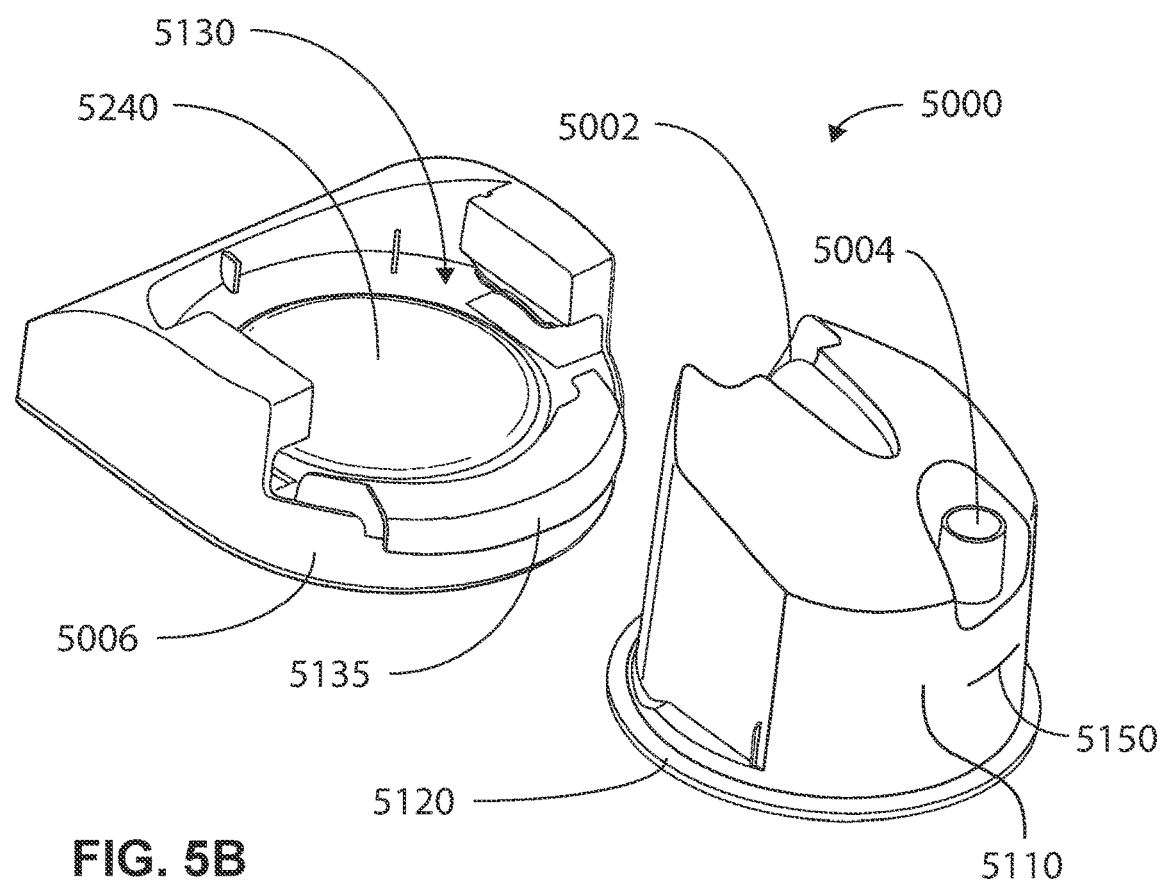
FIG. 5B shows an isometric view of a humidifier in accordance with one form of the present technology, showing a humidifier reservoir 5110 removed from the humidifier reservoir dock 5130.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Screening/Diagnosis/Monitoring Systems

5.7.1 Breathing waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 litres, inhalation time, Ti, 1.6 s, peak inspiratory flow rate, Qpeak, 0.4 L/s, exhalation time, Te, 2.4 s, peak expiratory flow rate, Qpeak, $-0.5$ L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot, is about 40%.

FIG. 6B shows patient data from a patient during non-REM sleep breathing normally over a period of about ninety seconds comprising about 34 breaths, being treated with Automatic PAP, and the mask pressure being about 11 cmH$_2$O. The top channel shows oximetry (oxygen saturation or SpO$_2$), the scale having a range of saturation from 90 to 99% in the vertical direction. The patient maintained a saturation of about 95% throughout the period shown. The second channel shows quantitative respiratory airflow, and the scale ranges from $-1$ to $+1$ litres per second in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electocardiogram. The seventh channel shows oxygen saturation with repetitive desaturations to below 70% from about 90%. The eighth channel is respiratory flow rate from a nasal cannula connected to a differential pressure transducer. Repetitive apneas of 25 to 35 seconds alternate with 10 to 15 second bursts of recovery breathing coinciding with EEG arousal and increased EMG activity. The ninth channel shows thoracic movement and the tenth shows abdominal movement. The abdomen shows a crescendo of movement over the length of the apnea leading to the arousal. Both become untidy during the arousal due to gross bodily movement during recovery hyperpnea. The apneas are therefore obstructive, and the condition is severe. The lowest channel is posture, and in this example it does not show change.

FIG. 6D shows patient flow rate data where the patient is experiencing a series of total obstructive apneas. The duration of the recording is approximately 160 seconds. Flow rates range from about +1 L/s to about −1.5 L/s. Each apnea lasts approximately 10 to 15 seconds.

FIG. 6E shows patient data from a patient with Cheyne-Stokes respiration. There are three channels: pulse oximetry ($SpO_2$); a signal indicative of flow rate; and thoracic movement. The data span six minutes. The signal representative of flow rate was measured using a pressure sensor connected to a nasal cannula. The patient exhibits apneas of about 22 seconds and hyperpneas of about 38 seconds. The higher frequency low amplitude oscillation in the flow rate signal during apnea is cardiogenic.

FIG. 6F shows patient data from a patient with another example of Cheyne-Stokes respiration, using the same three channels as in FIG. 6E. The data span ten minutes. The patient exhibits hyperpneas of about 30 seconds and hypopneas of about 30 seconds.

5.7.2 Polysomnography

FIG. 7A shows a patient 1000 undergoing polysomnography (PSG). The PSG system illustrated in FIG. 7A comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (thoracic movement sensor) 2040 on a chest band; a respiratory inductance plethysmogram (abdominal movement sensor) 2045 on an abdominal band; an oro-nasal cannula 2050 with oral thermistor; a photoplethysmograph (pulse oximeter) 2055; and a body position sensor 2060. The electrical signals from the electrodes (2015, 2020, 2025, 2030) are referenced to a ground electrode (ISOG) 2010 on the patient such as one positioned in the centre of the forehead.

5.7.3 Screening/Diagnosis/Monitoring Patch Device

FIG. 7B is a block diagram illustrating a screening/diagnosis/monitoring device 7100 according to one form of the present technology. The device 7100 may be configured as a patch, adapted to be worn on the skin of the chest of the patient 1000, preferably on the upper left chest.

The device 7100 comprises multiple biometric sensors 7170 to 7180, each configured to generate a signal representing one or more physiological parameters of a patient 1000. The ECG sensor 7170 comprises one or more electrical contacts which, when in contact with the skin, generate a signal known as the electrocardiogram (ECG or EKG) representative of the electrical activity of the heart. The three-axis accelerometer 7172 generates a three-component signal (referred to as the 3D accelerometry signal), each component of which represents the acceleration of the device 7100 along a corresponding orthogonal axis. In a typical orientation, the z-axis is perpendicular to the skin. The x- and y-axes may be aligned in any direction in the plane of the skin. However, the orientation of the x- and y-axes in relation to the main axes of the body (superior-inferior and medial-lateral) may be taken into account by the accelerometry signal analysis (described below). When the accelerometer 7172 is at rest, it can detect the influence of gravity and hence provide an absolute vertical direction. The photoplethysmograph (PPG or pulse oximeter) 7174 uses light to estimate the blood oxygen saturation ($SpO_2$, or oximetry) of the patient, usually represented as a percentage (%). The temperature sensor 7176 generates a signal representing the temperature of the patient's skin. The acoustic sensor 7178 (e.g. a microphone) generates a signal representing the heart sounds of the patient 1000. The galvanic skin response (GSR) sensor 7180 generates a signal representative of the conductivity of the skin in the region of the device 7100, which in turn is indicative of sympathetic nervous system activity (which among other physiological effects activates the sweat glands).

The device 7100 also comprises an input/output (I/O) interface such as a sensor interface 7160 (e.g., with multiple ports) that may receive the signals from the sensors 7170 to 7180 during a screening/diagnosis/monitoring session. The signals from the sensors may be generated by the sensors in analog or digital form. Thus, the interface may have analog and/or digital ports. For example, one or more of the sensor signals may arrive at the sensor interface 7160 as sequences of discrete samples ("sensor data") at respective sampling rates. The sensor interface 7160 may discretise those of the sensor signals not arriving in this form into respective sequences of discrete samples at respective sampling rates, so that all signals provided by the sensor interface 7160 are in discrete form.

In some cases, the device may be formed with or include a controller, such as a microcontroller with a processor or CPU. In some cases, the controller may be formed with a microprocessor. Thus, the device 7100 typically contains a processor 7110 configured to carry out the methods described herein such as with encoded instructions. The device 7100 may also contain a non-transient computer readable memory/storage medium 7130. The memory 7130 may be the internal memory of the device 7100, such as RAM, flash memory or ROM. In some implementations, memory 7130 may also be a removable or external memory linked to the device 7100, such as an SD card, server, USB flash drive or optical disc, for example. In other implementations, memory 7130 can be a combination of external and internal memory. The contents of the memory 7130 include stored data 7140 and processor control instructions (code) 7150 adapted to configure the processor 7110 to perform certain tasks. Stored data 7140 can include sensor data from sensor interface 7160 during a session, and other data that is provided as a component part of an application. Processor control instructions 7150 can also be provided as a component part of an application. The processor 7110 is adapted to read the code 7150 from the memory 7130 and execute the encoded instructions. In particular, the code 7150 may contain instructions that configure the processor 7110 to carry out methods of processing the sensor data signals from the sensor interface 7160. One such method may be to record the sensor data for the session in the memory 7130 as data 7140. Another such method may be to analyse the session recording to extract SDB features. One such analysis method is described in detail below. The processor 7110 may store the results of such analysis (the SDB features) as data 7140 in the memory 7130.

The device 7100 may also contain a communication interface 7120. The code 7150 may contain instructions adapted to configure the processor 7110 to communicate with a remote external computing device (not shown) such as an RPT device 4000 via the communication interface 7120. The mode of communication may be wired or wireless. In one such implementation, the processor 7110 may transmit the real time or session-by-session recording information from the data 7140 to the remote computing device via the communication interface 7120. In such an implementation, a processor of the remote computing device may be configured to analyse the received session recording to extract SDB features. In another such implementation, the processor 7110 may transmit the analysis results (e.g., indications of the SDB features or other detected or estimated patient related information) from the data 7140 to the remote computing device via the communication interface 7120. In yet another such implementation, the processor 7110 may partially analyse the session data, store and transmit the results of the partial analysis to the remote computing device via the communication interface 7120, and the processor of the remote computing device may complete the analysis to obtain the SDB features.

Alternatively, if the memory 7130 is removable from the device 7100, the remote computing device may be configured to be connected to the removable memory 7130. In such an implementation, the remote computing device may be configured to retrieve the session data from the removable memory 7130 and analyse the session data to extract SDB features.

In the case of transmission of data via the communication interface to an RPT device 4000, the data may serve as a basis for making control changes in an automated therapy adjustment process of the RPT device 4000 based on the data. For example, based on the extracted SDB features and/or sleep state, a therapy change, such as a change to pressure or flow (e.g., an increase or decrease) may be controlled by the RPT device 4000.

5.7.4 Signal Analysis

FIG. 8A is a flow chart illustrating example processes that may be implemented in a method 8000 of screening/diagnosing/monitoring SDB making use of the device 7100 in one form of the present technology. The method 8000 may be implemented by the processor 7110 of the device 7100, a processor of a remote external computing device in communication with the device 7100, or a combination of both as described above. The method 8000 may be carried out in real time during a session, in which case it is more appropriately described as a monitoring method, or in "batch" mode on recorded data after the session, in which case it is more appropriately described as a screening or diagnosis method.

Process 8005 removes movement and other artefacts from the ECG signal generated by the ECG sensor 7170. Process 8005 may optionally evaluate the 3D accelerometry signal from the accelerometer 7172 to detect timing of such artefacts for removal of corresponding portions of the ECG signal based on timing of such detection of artefacts. Such removal may include adjusting the ECG, such as by interpolation, smoothing or other technique, to produce an ECG signal that reduces or eliminates the effect of the artefact.

FIG. 8B is a flow chart illustrating an example method 8100 that may be implemented to perform the artefact removal process 8005 of the method 8000 in one form of the present technology. In this example, the method 8100 does not use the 3D accelerometry signal from the accelerometer 7172, but is based on the assumption that most portions of the ECG signal resemble the other portions, and identifies those portions that differ substantially from the typical. The method 8100 starts at process 8110, which band-pass filters the ECG signal such as within the frequency range of about 5 to 40 Hz. Process 8120 then differentiates (e.g., by derivative function) and squares the band-pass filtered ECG signal (e.g., by squaring function). The next process 8130 finds the upper envelope of the squared derivative of the band-pass filtered ECG signal.

Process 8140 then works sequentially through a sequence of non-overlapping windows of fixed duration into which the envelope is partitioned. In one implementation, the windows are of duration on the order of a predetermined number of seconds, (e.g., 30 seconds, 25 seconds, 35 seconds, etc.). For each window, process 8140 computes the autocorrelation function of the envelope, up to a lag of a predetermined number of samples (e.g., 45 samples). The next process 8150 computes a threshold by averaging the peak values of the autocorrelation functions over all windows, and dividing by a predetermined number (e.g., 10). Process 8150 then, for each window, sets those samples of the autocorrelation function whose values are less than the threshold to zero. Generally, the process 8150 removes small "noisy" values from the autocorrelation of each window, leaving only the "significant" features of the autocorrelation.

The final process 8160 determines whether each window contains artefacts. To do this, process 8160 compares the autocorrelation function (thresholded at process 8150) of a current window with the autocorrelation functions of a plurality of other windows (e.g., some or all other windows). In one implementation, the metric of comparison between two autocorrelation functions is the cosine function, computed as the dot product of the two autocorrelation functions divided by the product of their respective Euclidean norms. The cosine function ranges between 0 (for wholly dissimilar functions) and 1 (for identical functions). Process 8160 averages this metric for the similarity of the current window to other windows over the plurality of other windows to obtain a "normality" metric for the current window. If the normality metric for the current window falls below a threshold (e.g. 0.95), this indicates the current window is "outlying" enough to be discarded as an artefact.

FIG. 9 is a graph illustrating the operation of the method 8100 on an example ECG signal. The graph contains an ECG trace 9000 lasting approximately four minutes. Each vertical graticule shown in the bottom signal trace of FIG. 9 represents thirty seconds. The other traces 9010 to 9050 represent intermediate products of the method 8100 on the ECG trace 9000. The trace 9010 represents the band-pass filtered ECG from process 8110. The trace 9020 represents the derivative of the band-pass filtered ECG from process 8120. The trace 9030 represents the square of the derivative of the band-pass filtered ECG from process 8120. The trace 9040 represents the upper envelope of the square of the derivative of the band-pass filtered ECG from process 8130. The trace 9050 represents the "normality" metric of the envelope computed as part of process 8160. The binary-valued trace 9060 is high for "outlying" windows whose normality metric falls below 0.95, and 0 otherwise. It may be seen that the trace 9060 is high for two windows 9070 and 9080, both of which coincide with patterns of unusual activity in the ECG trace 9000, while the remainder of the ECG trace 9000 is relatively stationary.

Returning to the method 8000, the ECG signal, though primarily representative of heart activity, contains a component that is related to respiration. Process 8007 therefore extracts the respiratory-related component of the artefact-removed ECG signal, resulting in an EDR (ECG-derived respiratory) signal. In one implementation, process 8007 generates the EDR based on a determination of the amplitude of the R-wave of the ECG signal. In another implementation, process 8007 generates the EDR based on a determination of the area covered by the QRS complex of the ECG signal.

Process 8010 of the method 8000 evaluates the artefact-removed ECG signal to estimate the respiratory rate of the patient 1000. In one form, process 8010 applies a wavelet-based approach. In another form, process 8010 applies a combination of any two or more of differentiation, moving-average, and thresholding of the ECG signal.

Process 8015 evaluates the estimated respiratory rate from process 8010 and the artefact-removed ECG signal from process 8005 to detect the AFib burden of the patient (a measure of irregularity of the heart rhythm or atrial fibrillation and a classification of the type of irregularity: paroxysmal, persistent, or permanent).

Process 8020 removes artefacts from the 3D accelerometry signal generated by the accelerometer 7172. Process 8025 then evaluates the artefact-removed 3D accelerometry signal to estimate posture (e.g. prone, supine, upright), based on the absolute vertical direction provided by the accelerometer. For this step, the orientation of the axes of the accelerometer 7172 relative to the main axes of the body may be taken into account.

Process 8027 evaluates the artefact-removed 3D accelerometry signal to estimate respiratory effort. In one implementation, process 8027 applies a principal component analysis (PCA)-based method to the 3D accelerometry signal. For this step, the orientation of the axes of the accelerometer 7172 relative to the main axes of the body may be taken into account.

Process 8030 evaluates the artefact-removed 3D accelerometry signal to compute an activity index representative of the non-cardio-respiratory activity of the body, e.g. activity resulting from gross bodily motion.

Process 8035 segments the "heart sounds" acoustic signal from the acoustic sensor 7178. The segmentation partitions the acoustic signal into individual heart cycles and phases of each cycle (S1, systole, S2, diastole). Example implementations of process 8035 may apply any one or more of wavelet decomposition, Shannon energy, and peak location. Process 8040 then extracts heart sound features from the segmented heart sounds signal provided by the segmentation process 8035. Process 8040 may extract time domain features such as duration and amplitude, and frequency domain features such as power spectral density.

Processes 8005 to 8040 may be carried out in parallel or sequentially in any order, with the exceptions that process 8015 should follow processes 8005 and 8010, process 8007 should follow process 8005, processes 8025, 8027, and 8030 should follow process 8020, and process 8040 should follow process 8035.

Process 8045 evaluates the artefact-removed ECG signal from process 8005, the posture estimate from process 8025, the respiratory effort estimate from process 8027, the activity index from step 8030, the oxygen saturation (SpO$_2$) signal from the PPG 7174, the skin temperature signal from the temperature sensor 7176, and the sympathetic activity signal from the GSR sensor 7180 to estimate the sleep stage of the patient (e.g. wake, REM, non-REM (NREM)). Process 8045 may also detect brief arousals within the non-REM and REM stages. In one implementation, process 8045 extracts one or more features from its input signals, followed by classification such as by linear discriminant analysis (LDA), a support vector machine (SVM), or neural network to estimate the sleep stage and detect arousals.

Following process 8045, process 8050 evaluates the EDR signal and the respiratory rate estimate from processes 8005 and 8010, the posture estimate, the respiratory effort estimate, and the activity index from processes 8025, 8027, and 8030, and the SpO$_2$ signal from the PPG 7174 to detect SDB events, e.g., apneas and hypopneas (undifferentiated from each other). Process 8050 may also consider the estimated sleep stage from process 8045. In one implementation, process 8050 extracts features from its input signals and applies a classifier to the features to discriminate between normal breathing and SDB events in each of successive time windows, e.g. of duration 60 seconds or other predetermined window duration on the order of seconds or minutes.

Process 8060 classifies the detected SDB events from process 8050 into apneas and hypopneas, and into open airway and closed airway (obstructive) events, by evaluation of the SpO$_2$ signal from the PPG 7174, the sympathetic activity signal from the GSR sensor 7180, and the heart sound features extracted by process 8040. In one example of classification, an obstructive event may trigger sympathetic drive resulting in increased amplitude of heart sound(s) during the S1 phase of each heart cycle. An event coinciding with increased amplitude of heart sound(s) during the S1 phase of each heart cycle may therefore be classified as obstructive.

Process 8070 considers the detected events from process 8050 and their classifications from process 8060 and detects Cheyne-Stoke respiration (CSR) and (optionally) other forms of periodic breathing (PB). Process 8060 may be based on the sequencing and periodicity of the classified SDB events, and may also apply template matching of the EDR signal (from process 8005) during hyperpneas with a sinusoidal template in its evaluation.

From the classified SDB events from process 8060 and/or the CSR/PB detections from process 8070, various indices of SDB severity may be computed over a screening/diagnosis/monitoring session, e.g. apnea/hypopnea index (AHI), total duration of CSR episodes, etc. The computation of the indices may take into account the total sleep time (TST) of the patient during the session, as estimated from the sleep stage information provided by process 8045. The computed indices may be used for screening, diagnostic, or monitoring purposes in conventional fashion.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

Respiratory Pressure Therapy (RPT): The application of a supply of air to an entrance to the airways at a treatment pressure that is typically positive with respect to atmosphere.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate (respiratory rate): The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
    (i) Flattened: Having a rise followed by a relatively flat portion, followed by a fall.
    (ii) M-shaped: Having two local peaks, one at the leading edge, and one at the trailing edge, and a relatively flat portion between the two peaks.
    (iii) Chair-shaped: Having a single local peak, the peak being at the leading edge, followed by a relatively flat portion.
    (iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
    (i) a 30% reduction in patient breathing for at least 10 seconds plus an associated 4% desaturation; or
    (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9 Other Remarks

A portion of the disclosure of this patent document contains material which is subject to copyright protection.

The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 Reference Signs List patient 1000
bed partner 1100
headbox 2000
ground electrode 2010
EOG electrode 2015
EEG electrode 2020
ECG electrode 2025
submental EMG electrode 2030
snore sensor 2035
thoracic movement sensor 2040
abdominal movement sensor 2045
oro-nasal cannula 2050
photoplethysmograph 2055
body position sensor 2060
patient interface 3000
seal-forming structure 3100
plenum chamber 3200
structure 3300
vent 3400
connection port 3600
forehead support 3700
RPT device 4000
external housing 4010
upper portion 4012
portion 4014
panels 4015
chassis 4016
handle 4018
pneumatic block 4020
inlet air filter 4112
blower 4142
air circuit 4170
electrical components 4200
Printed Circuit Board Assembly 4202
electrical power supply 4210
input devices 4220
humidifier 5000
humidifier inlet 5002
humidifier outlet 5004
humidifier base 5006
humidifier reservoir 5110
humidifier reservoir dock 5130
heating element 5240
device 7100
processor 7110 communication interface 7120
memory 7130
data 7140
code 7150
sensor interface 7160
ECG sensor 7170
accelerometer 7172
PPG 7174
temperature sensor 7176
acoustic sensor 7178
GSR sensor 7180
method 8000
process 8005
process 8010
process 8015
process 8020
process 8025
process 8027
process 8030
process 8035
process 8040
process 8045
process 8050
process 8060
process 8070
method 8100
process 8110
process 8120
process 8130
process 8140
process 8150
process 8160
trace 9000
trace 9010
trace 9020
trace 9030
trace 9040
trace 9050
trace 9060
window 9070
window 9080

The invention claimed is:

1. A system comprising:
an electrocardiogram (ECG) sensor;
a respiratory therapy device comprising a controller configured to operate the respiratory therapy device for alleviating a respiratory disorder; and
one or more processors configured to:
remove artefacts from an ECG signal generated by the ECG sensor to produce artefact-removed ECG data, wherein the removing of the artefacts from the ECG signal comprises identifying portions of the ECG signal that differ from other portions of the ECG signal by comparing autocorrelation functions of a plurality of windows derived from the ECG signal;
analyze the artefact-removed ECG data, wherein the analyzing comprises (a) extracting an ECG-derived respiratory (EDR) signal from the artefact-removed ECG data or (b) estimating a respiratory rate from the artefact-removed ECG data; and
control an operation of the respiratory therapy device based on the analyzing of the artefact-removed ECG data for alleviating the respiratory disorder.

2. The system of claim 1, wherein a metric of comparison between two of the autocorrelation functions is a cosine function.

3. The system of claim 2, wherein the cosine function is computed as a dot product of the two autocorrelation functions divided by a product of their respective Euclidean norms.

4. The system of claim 1, wherein the one or more processors are further configured to detect an atrial fibrillation (AFib) burden of a patient based on the analyzing of the artefact-removed ECG data.

5. The system of claim 1, wherein the one or more processors are further configured to detect one or more sleep-disordered breathing (SDB) events based on the analyzing of the artefact-removed ECG data.

6. The system of claim 5, wherein the one or more processors are further configured to classify the one or more detected SDB events into apneas and hypopneas, and into open and closed airway events.

7. The system of claim 5, further comprising an accelerometer, wherein the one or more processors are further configured to analyze an accelerometry signal generated by the accelerometer, and wherein the detection of the one or more SDB events is also based on the analyzing of the accelerometry signal.

8. The system of claim 7, wherein the ECG sensor and the accelerometer are co-located in one device, and wherein the one device is configured as a patch adapted to be worn on skin of a chest of a patient.

9. The system of claim 1, wherein the controlling of the respiratory therapy device comprises an adjustment to an automated therapy.

10. The system of claim 1, wherein the respiratory therapy device is a respiratory pressure therapy (RPT) device, and wherein the controlling of the RPT device comprises an adjustment to a pressure or a flow generated by the RPT device.

11. The system of claim 1, wherein the respiratory disorder comprises sleep disordered breathing.

12. A system comprising:
an electrocardiogram (ECG) sensor;
a respiratory therapy device comprising a controller configured to operate the respiratory therapy device for alleviating a respiratory disorder; and
one or more processors configured to:
remove artefacts from an ECG signal generated by the ECG sensor to produce artefact-removed ECG data, wherein the removing of the artefacts from the ECG signal comprises:
filtering the ECG signal;
differentiating and squaring the filtered ECG signal;
finding an envelope of the squared derivative of the filtered ECG signal;
partitioning the envelope into a plurality of windows; and
computing an autocorrelation function for each of the windows;
analyze the artefact-removed ECG data, wherein the analyzing comprises (a) extracting an ECG-derived respiratory (EDR) signal from the artefact-removed ECG data or (b) estimating a respiratory rate from the artefact-removed ECG data; and
control an operation of the respiratory therapy device based on the analyzing of the artefact-removed ECG data for alleviating the respiratory disorder.

13. The system of claim 12, wherein each window has a fixed duration.

14. The system of claim 12, wherein the removing of the artefacts from the ECG signal further comprises:

computing a threshold by averaging peak values of the autocorrelation functions; and adjusting at least some samples of the autocorrelation functions based on comparisons between those samples and the threshold.

15. The system of claim 12, wherein the removing of the artefacts from the ECG signal further comprises comparing the autocorrelation functions to determine whether one or more of the plurality of windows contain artefacts.

16. The system of claim 12, wherein the respiratory therapy device is a respiratory pressure therapy (RPT) device, and wherein the controlling of the RPT device comprises an adjustment to a pressure or a flow generated by the RPT device.

17. The system of claim 16, further comprising the RPT device.

18. A method comprising:

removing, with one or more processors, artefacts from an electrocardiogram (ECG) signal generated by an ECG sensor to produce artefact-removed ECG data, wherein the removing of the artefacts from the ECG signal comprises identifying portions of the ECG signal that differ from other portions of the ECG signal by comparing autocorrelation functions of a plurality of windows derived from the ECG signal;

analyzing, with the one or more processors, the artefact-removed ECG data, wherein the analyzing comprises (a) extracting an ECG-derived respiratory (EDR) signal from the artefact-removed ECG data or (b) estimating a respiratory rate from the artefact-removed ECG data; and controlling, with the one or more processors, an operation of a respiratory therapy device based on the analyzing of the artefact-removed ECG data for alleviating the respiratory disorder.

19. A non-transitory computer readable storage medium having instructions stored thereon that, when executed by one or more processors, cause the one or more processors to perform the method of claim 18.

20. The method of claim 18, wherein the respiratory therapy device is a respiratory pressure therapy (RPT) device, and wherein the controlling of the RPT device comprises an adjustment to a pressure or a flow generated by the RPT device.

* * * * *